United States Patent [19]

Farge et al.

[11] 4,347,359

[45] Aug. 31, 1982

[54] 1,2,4-TRIAZINES

[75] Inventors: Daniel Farge; Pierre Le Roy, both of Thiais; Claude Moutonnier, Le Plessis Robinson; Jean-Francois Peyronel, Palaiseau, all of France

[73] Assignee: Rhone-Poulenc Industries, France

[21] Appl. No.: 225,446

[22] Filed: Jan. 15, 1981

[30] Foreign Application Priority Data

Jan. 17, 1980 [FR] France ............................ 80 00979
May 13, 1980 [FR] France ............................ 80 10708

[51] Int. Cl.³ .............................................. C07D 253/06
[52] U.S. Cl. .................................................... 544/182
[58] Field of Search ........................................ 544/182

[56] References Cited

FOREIGN PATENT DOCUMENTS 2100834 3/1972 France .
2249882 5/1975 France .
2280381 2/1976 France .
2370053 6/1979 France .

*Primary Examiner*—John M. Ford
*Attorney, Agent, or Firm*—Stevens, Davis, Miller & Mosher

[57] ABSTRACT

New thiols of the general formula:

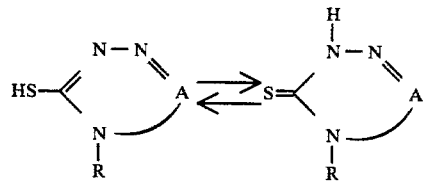

wherein A represents a 2-hydroxy-1-oxoethan-1-yl-2-ylidene or alkoxycarbonylmethyne radical or a nitrogen atom and R represents various substituted alkyl radicals, and their alkali metal and alkaline earth metal salts are useful as intermediates in the preparation of cephalosporins having anti-bacterial properties.

12 Claims, No Drawings

1,2,4-TRIAZINES

DESCRIPTION

This invention relates to new thiols, useful as intermediates in the preparation of anti-bacterial cephalosporins and to processes for their preparation.

The present invention provides new thiols (which may exist in their tautomeric form) of the general formula:

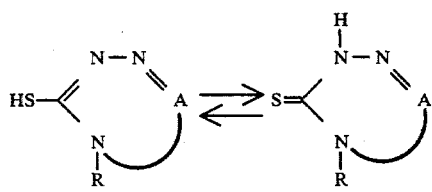

wherein the symbol =A— represents a nitrogen atom or a trivalent radical selected from 2-hydroxyl-1-oxoethan-1-yl-2-ylidene (IIa) and alkoxycarbonylmethyne (IIb), i.e.

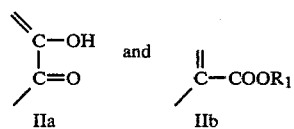

(wherein $R_1$ represents an alkyl radical) and (1) and A represents a radical IIa, R represents:

(a) a 2,3-dihydroxypropyl or 1,3-dihydroxyprop-2-yl radical, protected in the form of a 2,2-dimethyldioxolan-4-yl-methyl or 2,2-dimethyldioxan-5-yl radical, respectively;

(b) an alkyl radical containing 2 to 4 carbon atoms, which is substituted by an alkylsulphonylamino or sulphamoylamino radical, an acylamino radical (in which the acyl moiety is substituted by hydroxy, amino, alkylamino or dialkylamino), or an alkoxycarbonylamino, ureido, alkylureido or dialkylureido radical;

(c) an alkyl radical containing 2 to 5 carbon atoms, which is substituted by an alkoxyimino or hydroxyimino radical, (d) a radical of the general formula:

wherein alk represents an alkylene radical containing 1 to 4 carbon atoms, $X^\alpha$ and $Y^\alpha$ are identical and represent oxygen or sulphur atoms and $R^\alpha$ represents an alkyl radical, or $X^\alpha$ and $Y^\alpha$ are identical or different and represent oxygen or sulphur atoms and the radicals $R^\alpha$ together form an alkylene radical containing 2 or 3 carbon atoms, and $R^\beta$ represents an alkyl radical containing 1 to 3 carbon atoms;

(e) a carbamoyloxyalkyl, alkylsulphinylalkyl or alkylsulphonylalkyl radical, in which the alkyl moiety bonded to the triazine grouping in general formula I contains 2 to 4 carbon atoms;

(f) a phenylalkyl or alkylthioalkyl radical; or (g) a radical of the general formula:

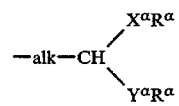

wherein alk, $X^\alpha$, $Y^\alpha$ and $R^\alpha$ are as hereinbefore defined; or (2) when A represents a radical IIb, R represents a radical defined above in (1) (a), (b), (c) or (d); or (3) when A represents a nitrogen atom, R represents:

(a) a 1,3-dihydroxyprop-2-yl radical which is free or protected in the form of a 2,2-dimethyldioxan-5-yl radical, or (b) a radical IIIb or IIIc as hereinbefore defined;

and alkali metal and alkaline earth metal salts thereof.

It is to be understood that alkyl and acyl moieties or radicals in this specification and the accompanying claims are linear or branched and unless otherwise specified contain from 1 to 4 carbon atoms.

When the symbol A represents a radical IIa the compounds of general formula I are triazines which exist in various tautomeric forms. When the radical R represents a hydroxyiminoalkyl or alkoxyiminoalkyl radical such radicals can exhibit syn/anti isomerism and these isomers and the various tautomeric forms and their mixtures are within the scope of the present invention. The tautomeric forms of triazines, for example of 3-thioxo-4-methyl-5,6-dioxo-hexahydro-1,2,4-triazine, are described below.

3-Thioxo-4-methyl-5,6-dioxo-hexahydro-1,2,4-triazine and N-methyl-3-mercapto-5-ethoxycarbonyl-1,2,4-triazole, and their preparation from 4-methylthiosemicarbazide and the diethyl ester of oxalic acid, have been described in C.R. Acad. Sci., Ser. C, 267, 25, 1,726 (1968).

3-Thioxo-4-methyl-5,6-dioxo-hexahydro-1,2,4-triazine and its tautomeric forms:

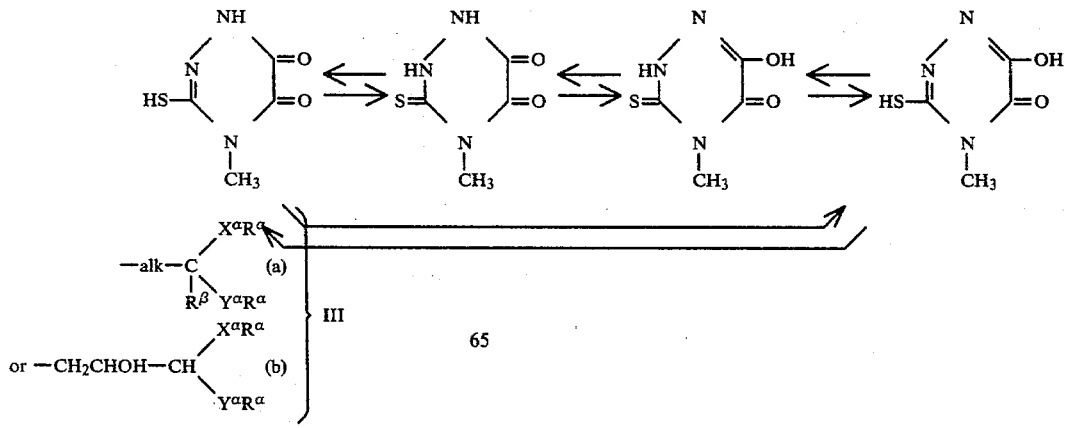

have been described in Bull. Soc. Chim., 4, 1,599 (1970).

5,6-Dioxo-3-mercaptotriazines substituted in the 4-position by alkyl, allyl and 2-methoxyethyl radicals, which are intermediates for the synthesis of cephalosporins, have been described in the published French Patent Application No. 2,275,215.

Triazines of the general formula:

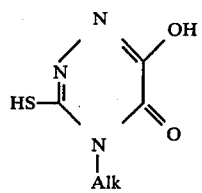

in which Alk is an alkyl group, which are intermediates for the synthesis of cephalosporins, have been described in Belgian Pat. No. 872,616.

According to a feature of the present invention, the compounds of general formula I wherein A represents a radical IIa or IIb and R is as hereinbefore defined can be prepared by reacting a thiosemicarbazide of the general formula:

R—NH CS NH NH$_2$   IV (wherein R is as hereinbefore defined, it being understood that, when R contains an amino or alkylamino radical, that radical may be protected) and an oxalic acid derivative of the general formula:

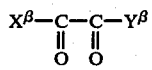

(wherein $X^\beta$ and $Y^\beta$ are identical or different and represent chlorine atoms or linear or branched alkoxy radicals containing 1 to 4 carbon atoms), in the presence of an alkali metal alkoxide in the corresponding alcohol (e.g. sodium ethoxide or methoxide in ethanol or methanol respectively, or potassium t-butoxide in t-butanol). The reaction is advantageously carried out at the reflux temperature of the reaction mixture.

If it is desired to prepare a compound of general formula I wherein A represents the 2-hydroxy-1-oxoethan-1-yl-2-ylidene radical, the reaction is preferably carried out in the presence of two equivalents of the alkali metal alkoxide in the corresponding alcohol. The alkali metal salt is generally isolated directly by crystallisation or, if appropriate, the thiol is isolated by chromatography or crystallisation, after acidification of the reaction mixture and extraction.

If it is desired to prepare a compound of general formula I wherein A represent an alkoxycarbonylmethyne radical, the reaction is preferably carried out in the presence of one equivalent of the alkali metal alkoxide in the corresponding alcohol. The mercaptotriazole product is generally isolated after acidification and extraction either of the reaction mixture or of the mother liquors (if the salt of the corresponding triazine has crystallised), followed by chromatography of the resulting solution.

According to a further feature of the invention, the compounds of general formula I can also be prepared by reacting an isothiocyanate or a dithiocarbamate of the general formula:

R—Z   VI (wherein R is as hereinbefore defined, it being understood that, when R contains an amino or alkylamino radical, that radical may be protected, and Z represents an isothiocyanato radical or a radical of the general formula:

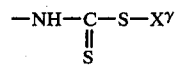

wherein $X^\gamma$ is a linear or branched alkyl radical containing 1 to 4 carbon atoms) either (a) with a compound of the general formula:

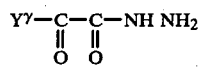

(wherein $Y^\gamma$ represents a linear or branched alkoxy radical containing 1 to 4 carbon atoms, or an amino, alkylamino or dialkylamino radical) in the presence of a basic reagent, if it is desired to prepare a compound of general formula I wherein A represents a radical IIa or IIb, or (b) with sodium nitride if it is desired to prepare a compound of general formula I wherein A represents a nitrogen atom.

It is to be understood that, when R represents a 1,3-dihydroxyprop-2-yl radical, it is necessary, before the reaction, to protect it in the form of a cyclic acetal, i.e. as the 2,2-dimethyldioxan-5-yl radical. The 1,3-dihydroxyprop-2-yl radical is regenerated by acid hydrolysis after the reaction. The regeneration is carried out, e.g. by means of trifluoroacetic acid, aqueous or non-aqueous formic acid, para-toluenesulphonic acid or methanesulphonic acid.

If it is desired to obtain a compound of general formula I wherein A represents a radical IIa or IIb, the reaction is generally carried out under the conditions described above for the reaction of compounds of general formulae IV and V.

It is desired to obtain a compound of general formula I wherein A represents a nitrogen atom, the reaction is generally carried out in an aqueous or aqueous-organic medium or in a water-miscible solvent [such as an alcohol (e.g. methanol or ethanol), acetonitrile, acetone or dimethylformamide], at a temperature between 60° C. and the reflux temperature of the reaction mixture.

The thiosemicarbazides of general formula IV and the compounds of general formula VI can be prepared by applying one of the methods described by K. A. Jensen et al., Acta Chem. Scand., 22, 1 (1968), or by applying the method described by Y. Kazakov and J. Y. Potovskii, Doklady Acad. Nauk. SSSR, 134, 824 (1960), it being understood that, when R contains an amino or alkylamino radical, that radical is protected by known methods. Furthermore:

the compounds of general formula VI can also be obtained by applying the methods described in Houben Weyl, Volume 9, pages 837–45 and pages 869–78 [G. Thieme Verlag Stuttgart (1955)];

when R represents phenylalkyl, the thiosemicarbazide of general formula IV can be prepared by applying the method described by W. Baird et al., J. Chem. Soc., 2,527 (1927);

when R represents alkylthioalkyl, the thiosemicarbazide of general formula IV can be prepared by reacting hydrazine hydrate with methyl N-(alkylthioalkyl)-dithiocarbamate in ethanol, at the reflux temperature of the reaction mixture; and when R represents a radical of general formula IIIc, the thiosemicarbazide of general formula IV can be prepared by reacting hydrazine hydrate with the corresponding isothiocyanate in ethanol, at a temperature between 0° and 10° C.

By the expression "known methods" as used in this specification is meant methods heretofore used or described in the literature.

The protection of the amino or alkylamino groups which may be carried by R (and the removal of the protecting radical from the said groups) is carried out in accordance with known methods which do not affect the rest of the molecule. The t-butoxycarbonyl group, which can be removed by acid hydrolysis, is particularly useful.

The compounds of general formula VIII have been described by M. Pesson and M. Antoine, Bull. Soc. Chim. France, 4, 1,599 (1970).

The new compounds of general formula I and their salts are useful, in particular, as intermediates for the preparation of cephalosporins of the general formula:

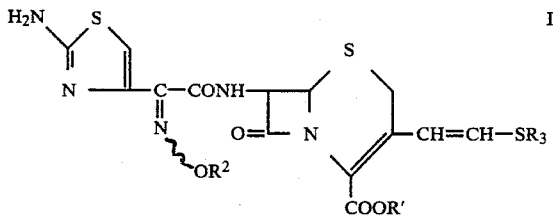

wherein $R^2$ represents a hydrogen atom or an alkyl, vinyl or cyanomethyl radical, R' represents a hydrogen atom or a radical, which can easily be removed by an enzymatic method, of the general formula:

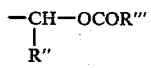

wherein R" represents a hydrogen atom or an alkyl radical and R''' represents an alkyl radical or the cyclohexyl radical, and (1') $R_3$ represents a 5,6-dioxo-1,4,5,6-tetrahydro-1,2,4-triazin-3-yl radical substituted in the 4-position by:

(a) a 2,3-dihydroxypropyl or 1,3-dihydroxyprop-2-yl radical, (b) an alkyl radical containing 2 to 4 carbon atoms, which is substituted by an amino, alkylsulphonylamino or sulphamoylamino radical, an acylamino radical (in which the acyl moiety is substituted by hydroxy, amino, alkylamino or dialkylamino), or an alkoxycarbonylamino, ureido, alkylureido or dialkylureido radical, (c) an alkyl radical containing 2 to 5 carbon atoms, which is substituted by an alkoxyimino or hydroxyimino radical, (d) a radical of general formula IIIa or IIIb, (e) an acylalkyl or 2-formyl-2-hydroxyethyl radical, (f) a carbamoyloxyalkyl, alkylsulphinylalkyl or alkylsulphonylalkyl radical in which the alkyl moiety bonded to the triazine ring contains 2 to 4 carbon atoms, (g) a phenylalkyl or alkylthioalkyl radical, or (h) a radical of general formula IIIc: (2') $R_3$ represents a 2-alkoxycarbonyl-1,3,4-triazol-5-yl radical substituted in the 1-position by a radical defined above in (1') (a), (b), (c), (d) or (e); or (3') $R_3$ is a tetrazol-5-yl radical substituted in the 1-position by:

(a) a 1,3-dihydroxyprop-2-yl radical, (b) a radical of general formula IIIb or IIIc as hereinbefore defined, or (c) a formylalkyl or 2-formyl-2-hydroxyethyl radical.

The substituent in the 3-position of the compounds of general formula IX can exist in the cis or trans form or as a mixture of the cis and trans forms.

In the following text, the trans stereoisomer is designated by E and the cis stereoisomer is designated by Z.

Furthermore, the $OR^2$ group can be in either the syn or anti configuration and these isomers and their mixtures can be prepared from the compounds of the present invention.

The syn form can be represented by the general formula:

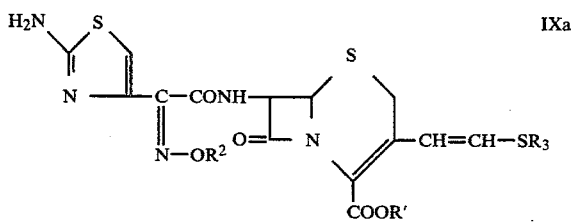

and the anti form by the general formula:

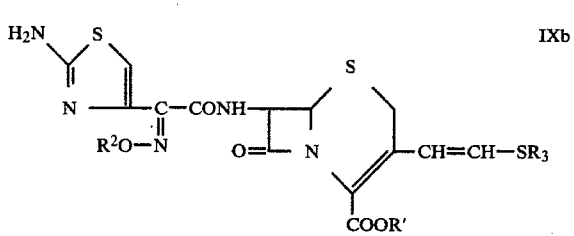

wherein the various symbols are as hereinbefore defined.

Furthermore, when the radical $R_3$ contains a formylalkyl radical, it can exist in the form of the free aldehyde or the aldehyde hydrate.

The compounds according to the invention can be used in the following manner:

A compound of general formula I or an alkali metal or alkaline earth metal salt thereof, wherein R is as hereinbefore defined, is reacted with a cephalosporin derivative of the general formula:

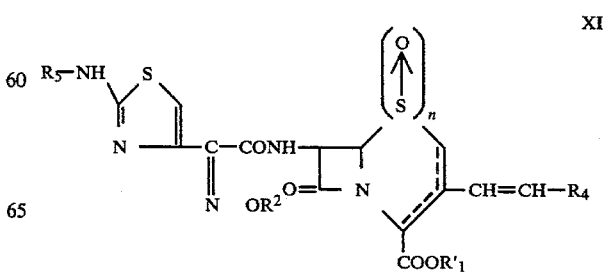

(or a mixture of the isomers of this derivative), wherein $R^2$ is as hereinbefore defined, $R'_1$ is as defined for $R'$ or represents a protecting radical which can be easily removed, e.g. methoxymethyl, t-butyl, benzhydryl, p-nitrobenzyl or p-methoxybenzyl, n represents 0 or 1 (if n=0, the product is in the form of a bicyclooct-2-ene or -3-ene and if n=1, the product is in the form of a bicyclooct-2-ene, according to the nomenclature of Chemical Abstracts), the substituent on the carbon atom in the 3-position of the bicyclooctene exhibits E/Z stereoisomerism, $R_4$ represents a radical of the general formula:

$$-O-SO_2-R'_4 \qquad \qquad \text{XII}$$

$$\text{or} -O-CO-R''_4 \qquad \qquad \text{XIII}$$

(wherein $R'_4$ represents an alkyl, trifluoromethyl or trichloromethyl radical or a phenyl radical optionally substituted by a halogen atom or by an alkyl or nitro radical, and $R''_4$ is as hereinbefore defined for $R'_4$ or represents an acylmethyl, 2-acylethyl, 2-acylpropyl, alkoxycarbonylmethyl, 2-alkoxycarbonylethyl or 2-alkoxycarbonylpropyl radical) and $R_5$ represents a hydrogen atom or an amino-protecting group, which can be easily removed, such as a t-butoxycarbonyl, 2,2,2-trichloroethoxycarbonyl, chloroacetyl, trichloroacetyl, trityl, benzyl, dibenzyl, benzyloxycarbonyl, p-nitrobenzyloxycarbonyl, p-methoxybenzyloxycarbonyl, formyl or trifluoroacetyl group, and the resulting oxide (if n=1) is then reduced and, if necessary, protecting radicals are removed.

It is to be understood that, if $R^2$ represents hydrogen, it is necessary to protect the oxime. The oxime can be protected by any known method which does not affect the rest of the molecule. Trityl, tetrahydropyranyl or 2-methoxyprop-2-yl groups, which can be removed by acidolysis, e.g. by means of trifluoroacetic acid, aqueous or non-aqueous formic acid or para-toluenesulphonic acid, are particularly useful. The removal of these groups can be carried out equally well before, simultaneously with or after that of the other protecting radicals.

It is also to be understood that, if the compound of general formula I contains a group which is capable of interfering with the reaction, it is preferable to protect this group (in particular if it contains an amino, alkylamino or hydroxy radical).

Furthermore, if the compound of general formula I contains a substituent which is capable of interfering with the reduction reaction, it is preferable to use a compound of general formula XI in which n=0 (in particular if it contains a hydroxy or sulphonyl radical).

If it is desired to obtain a compound of general formula IX in which $R_3$ contains a formylalkyl or acylalkyl radical, the corresponding thiol in which this radical is protected in the form of an acetal of general formula IIIa, IIIb or IIIc is reacted, and the protecting radical is then removed.

If it is desired to obtain a compound of general formula IX in which $R_3$ is substituted by an aminoalkyl radical, the corresponding thiol of general formula I in which this radical is protected by a t-butoxycarbonyl radical is reacted, and the protecting radical is then removed after the reaction.

The reaction is generally carried out in the presence of an organic base, such as a pyridine or a tertiary organic base of the general formula:

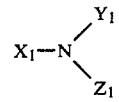

wherein $X_1$, $Y_1$ and $Z_1$, which may be the same or different, represent alkyl or phenyl radicals or two of them form a ring together with the nitrogen atom to which they are attached. Examples of tertiary organic bases used are diisopropylethylamine or diethylphenylamine.

The reaction is advantageously carried out in an organic solvent, such as dimethylformamide, tetrahydrofuran or acetonitrile or in a mixture thereof.

It is also possible to carry out the reaction in the presence of an alkali metal bicarbonate, in an organic solvent, e.g. as mentioned above, if appropriate in the presence of water.

The reaction is generally carried out at a temperature from $-20°$ C. to the reflux temperature of the reaction mixture, the chosen temperature varying according to the thiol employed. Likewise, depending on the thiol employed, the reaction time can vary from 5 minutes to 48 hours.

If appropriate, the reaction is carried out under a nitrogen atmosphere.

If an alkali metal salt or alkaline earth metal salt of the compound of general formula I is used, it is preferable to use a cephalosporin of general formula XI in which n=0 and, furthermore, it is not necessary to carry out the reaction in the presence of an organic base as defined above.

Preferably, if it is desired to use a bicyclooct-3-ene of general formula XI, a compound of this type in which $R'_1$ is other than hydrogen is used.

The reduction of the S-oxide can be carried out under the conditions described in published German Patent Application 2,637,176.

Depending on the nature of the protecting groups, they can be removed simultaneously or successively in accordance with known methods.

By way of example:

1. The amino-protecting groups are removed:

(a) in the case of a t-butoxycarbonyl, trityl, p-methoxybenzyloxycarbonyl or formyl radical: by treatment in an acid medium. The acid used is preferably trifluoroacetic acid, the reaction being carried out at a temperature between 0° and 20° C. Anhydrous or aqueous formic acid, or para-toluenesulphonic acid or methanesulphonic acid may also be used, the reaction then being carried out in acetone at the reflux temperature of the reaction mixture. Under these conditions, the compound of general formula IX can be obtained in the form of the trifluoroacetate, the solvate with formic acid, the methanesulphonate or the para-toluenesulphonate, from which the amine group can be freed by any known method for obtaining an amine from one of its salts without affecting the rest of the molecule. The reaction is preferably carried out by bringing the product into contact with an ion exchange resin or by reacting it with an organic base;

(b) in the case of a 2,2,2-trichloroethoxycarbonyl or p-nitrobenzyloxycarbonyl radical: by reduction (in particular by treatment with zinc in acetic acid);

(c) in the case of a chloroacetyl or trichloroacetyl radical: by applying the method described in the published French Patent Application No. 2,243,199;

(d) in the case of a benzyl, dibenzyl or benzyloxycarbonyl radical: by catalytic hydrogenation; or (e) in the case of a trifluoroacetyl radical: by treatment in a basic medium.

2. The carboxy-protecting groups are removed:

(a) in the case of a t-butyl, p-methoxybenzyl or benzhydryl group: by treatment in an acid medium, under the conditions described above for the removal of the trityl amino-protecting group. In the case of the benzhydryl radical, the reaction can be carried out in the presence of anisole;

(b) in the case of a methoxymethyl group: by treatment in a dilute acid medium; or (c) in the case of a p-nitrobenzyl group: by reduction (preferably by treatment with zinc in acetic acid or by hydrogenation).

3. The groups protecting the oxime and/or the hydroxy radicals are removed:

(a) in the case of a trityl or tetrahydropyranyl group or of the 2,2-dimethyldioxolan-4-yl-methyl or 2,2-dimethyldioxan-5-yl radicals: by acid hydrolysis, e.g. by means of trifluoroacetic acid, aqueous or non-aqueous formic acid or para-toluenesulphonic acid; or (b) in the case of the 2-methoxyprop-2-yl group: in accordance with the method described in Belgian Pat. No. 875,379.

4. The protecting groups in the radicals of general formula IIIb, IIIc or IIIa (if it is desired to obtain a product of the general formula IX in which $R_3$ contains a formylalkyl or acylalkyl radical) are removed:

(a) in the presence of a sulphonic acid (e.g. methanesulphonic acid or p-toluenesulphonic acid), in an organic solvent (e.g. acetonitrile or acetone), if appropriate in the presence of water and if appropriate in the presence of a reactant which can be converted to an acetal, such as acetone, glyoxylic acid, benzaldehyde or pyruvic acid, at a temperature from 20° C. to the reflux temperature of the reaction mixture; or alternatively (b) if the radical $R_3$ is a 5,6-dioxo-1,4,5,6-tetrahydro-1,2,4-triazin-3-yl radical substituted in the 4-position by a formylalkyl or acylalkyl radical, by aqueous formic acid (preferably containing less than 10% v/v of water), either in the presence or absence of silica or by transacetalisation in the presence of a reactant which can be converted to an acetal, as defined above.

The compounds of general formula I can also be used to prepare the cephalosporins of general formula IX in accordance with the following procedure:

A compound of the general formula:

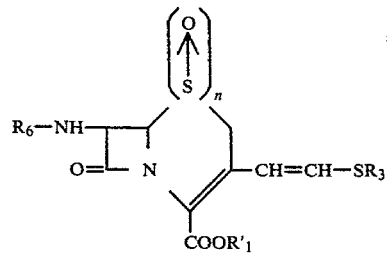

XV wherein $R'_1$, $R_3$ and n are as hereinbefore defined and $R_6$ is a radical which can be easily removed, is prepared by reacting a compound of general formula I with a cephalosporin derivative (or with a mixture of its isomers) of the general formula:

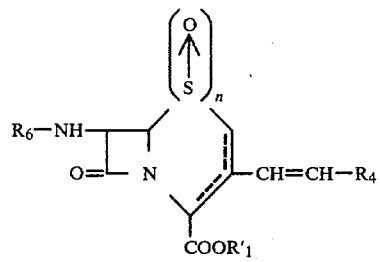

XVI wherein $R'_1$, $R_4$, $R_6$ and n are as hereinbefore defined, and when n is 0, the compound is in the form of a bicyclooct-2-ene or -3-ene, when n is 1, the compound is in the form of a bicyclooct-2-ene, and the substituent on the carbon atom in the 3-position of the bicyclooctene exhibits E/Z stereoisomerism.

It is to be understood that the radicals $R_6$ which can be easily removed are a benzhydryl or trityl radical, a 2,2,2-trichloroethyl radical, an acyl radical of the general formula:

$R_7$—CO—            XVII

[wherein $R_7$ represents a hydrogen atom, an alkyl radical (which is optionally substituted by one or more halogen atoms or by a phenyl or phenoxy radical) or a phenyl radical] or a radical of the general formula:

$R_8$ O CO—            XVIII

[wherein $R_8$ represents an unsubstituted branched alkyl radical, a linear or branched alkyl radical carrying one or more substituents selected from halogen atoms and a cyano, trialkylsilyl or phenyl radical or a phenyl radical which is substituted by one or more alkoxy, nitro or phenyl radicals, or represents a vinyl, allyl or quinolyl radical[ or a nitrophenylthio radical. Furthermore, the radical $R_6NH$- can be replaced by a methyleneimino radical in which the methylene radical is substituted by a dialkylamino or aryl group (the latter group being optionally substituted by one or mre methoxy or nitro radicals).

The following radicals may, for example, be used as radicals $R_6$: formyl, acetyl, chloroacetyl, trichloroacetyl, phenylacetyl, phenoxyacetyl and benzoyl; t-butoxycarbonyl; 2-chloro-1,1-dimethylethoxycarbonyl; 2,2,2-trichloroethoxycarbonyl; 2,2,2-trichloro-1,1-dimethylethoxycarbonyl; 2-cyano-1,1-dimethylethoxycarbonyl; 2-trimethylsilylethoxycarbonyl; benzyloxycarbonyl; p-methoxybenzyloxycarbonyl; 3,5-dimethoxybenzyloxycarbonyl; p-nitrobenzyloxycarbonyl; diphenylmethoxycarbonyl; 2-(biphenyl-4-yl)-isopropoxycarbonyl; vinyloxycarbonyl; allyloxycarbonyl; quinol-8-yloxycarbonyl; o-nitrophenylthio; and p-nitrophenylthio.

Examples of methyleneimino radicals are dimethylaminomethyleneimino, 3,4-dimethoxybenzylideneimino and 4-nitrobenzylideneimino.

The reaction of the compounds of general formulae I and XVI is generally carried out under the conditions described above for the preparation of a 3-thiovinylcephalosporin of general formula IX from a thiol of general formula I and a compound of general formula XI.

A compound of the general formula:

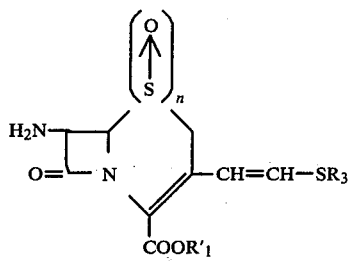

XIX wherein R'₁, R₃ and n are as hereinbefore defined, is prepared by removing the radical R₆, or simultaneously removing the protecting radicals R₆ and R'₁, from the compound of general formula XV, wherein R'₁, R₃, R₆ and n are as hereinbefore defined.

The protecting radical R₆ is removed by any known method for freeing an amine group without affecting the rest of the molecule.

The following are examples of suitable methods:

when R₆ represents trityl, benzhydryl, trichloroacetyl, chloroacetyl, t-butoxycarbonyl, trichloroethoxycarbonyl, benzyloxycarbonyl, p-methoxybenzyloxycarbonyl or p-nitrobenzyloxycarbonyl: in accordance with the abovementioned methods for freeing the amino radical of the product of the general formula IX;

when R₆ represents formyl, 2-chloro-1,1-dimethylethoxycarbonyl, 2-cyano-1,1-dimethylethoxycarbonyl, 3,5-dimethoxybenzyloxycarbonyl, diphenylmethoxycarbonyl, 2-(biphenyl-4-yl)-isopropoxycarbonyl, vinyloxycarbonyl, allyloxycarbonyl, quinol-8-yl-oxycarbonyl, o-nitrophenylthio or p-nitrophenylthio, and if R₆NH- is replaced by dimethylaminomethyleneimino, 3,4-dimethoxybenzylideneimino or 4-nitrobenzylideneimino: by hydrolysis in an acid medium;

when R₆ represents 2,2,2-trichloroethyl or 2,2,2-trichloro-1,1-dimethylethoxycarbonyl: by treatment with zinc in acetic acid;

when R₆ represents acetyl, benzoyl, phenylacetyl or phenoxyacetyl: in accordance with the method described in Belgian Patent No. 758,800;

when R₆ represents trimethylsilylethoxycarbonyl: in accordance with the method described by H. Gerlach, Helv. Chim. Acta, 60 (8), 3,039 (1977); or when R₆ represents p-nitrobenzyloxycarbonyl: by hydrogenation in the presence of palladium.

A compound of general formula IX as hereinbefore defined is then prepared by reacting the compound of general formula XIX with an acid of the general formula:

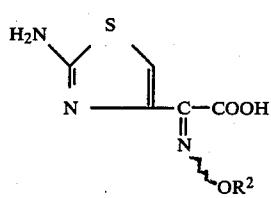

XX (wherein R² is as hereinbefore defined) in which the amine group has been protected beforehand (as well as the oxime group if R² represents a hydrogen atom), or with a reactive derivative of the acid, reduction of the resulting sulphoxide (if n=1), and removal of the protecting radicals. Suitable reactive derivatives are described hereinafter in general formula XXI.

It is to be understood that the acid of general formula XX in the syn or anti form, or mixtures thereof, leads to the compounds of general formula IX in the syn or anti form, or mixtures thereof, respectively.

The amino group in the compound of formula XX may be protected by any known method for blocking an amine group without affecting the rest of the molecule. A protecting radical as hereinbefore defined for R₅ is generally used.

If R² represents a hydrogen atom, the oxime is protected under the conditions described above for the compound of general formula IX.

The condensation of the compound of general formula XX, in which the acid group is free and in which the amine group has been protected beforehand, with the 7-aminocephalosporin of general formula XIX, in which R₃ and n are as hereinbefore defined and R'₁ represents a radical of general formula X or a protecting radical which can be easily removed, such as methoxymethyl, t-butyl, benzhydryl, p-nitrobenzyl or p-methoxybenzyl, is generally carried out in an organic solvent, such as dimethylformamide, acetonitrile, tetrahydrofuran, methylene chloride or chloroform, in the presence of a condensation agent, such as a carbodiimide (e.g. dicyclohexylcarbodiimide), N,N'-carbonyldiimidazole or 2-ethoxy-1-ethoxycarbonyl-1,2-dihydroquinoline, at a temperature from −20° to 40° C., the resulting oxide is then reduced if a 7-aminocephalosporin of general formula XIX in which n=1 has been used, and the protecting groups are removed.

It is to be understood that the amino, alkylamino or hydroxy groups which exist in certain radicals R₃ are, or can be, protected by any protecting groups which are normally used to protect amines or alcohols, and the use of which does not affect the rest of the molecule.

By ay of example:

the amino and alkylamino groups may be protected by radicals such as t-butoxycarbonyl, 2,2,2-trichloroethoxycarbonyl, trichloroacetyl, trityl, benzyl, dibenzyl, benzyloxycarbonyl, p-nitrobenzyloxycarbonyl, p-methoxybenzyloxycarbonyl, chloroacetyl, formyl or trifluoroacetyl; and the hydroxy groups can be protected by radicals such as trityl, tetrahydropyranyl or 2-methoxyprop-2-yl, or alternatively in the form of a 2,2-dimethyldioxan-5-yl radical when the 1,3-dihydroxyprop-2-yl radical is protected.

It is also to be understood that, when the radical R₃ in general formula XIX contains a free hydroxy group or a sulphonyl group, it is preferable to use a compound in the formula of which n=0.

If it is desired to obtain a compound of general formula IX in which R₃ contains a formylalkyl or acylalkyl radical, this radical is optionally protected in the form of an acetal, i.e. as a radical of general formula IIIa, IIIb or IIIc as hereinbefore defined.

Protecting radicals in R₃ are removed after the reduction of the oxide, before, simultaneously with or after the removal of other protecting radicals.

The reduction of the S-oxide is carried out e.g. under conditions hereinbefore described.

If a reactive derivative of the acid of general formula XX is used, it is possible to use the anhydride, a mixed anhydride or a reactive ester of the general formula:

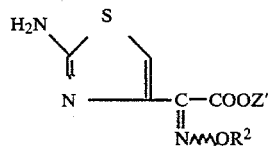 XXI wherein $R^2$ is as hereinbefore defined and $Z'$ represents a succinimido, benzotriazol-1-yl, 4-nitrophenyl, 2,4-dinitrophenyl, pentachlorophenyl or phthalimido radical, and in which the amine group has been protected beforehand (e.g. by a protecting group such as those mentioned above for $R_5$). It is also possible to use an acid halide, e.g. the acid chloride, in particular by reacting the hydrochloride of the chloride of the acid of general formula XX with the 7-aminocephalosporin of general formula XIX.

If the anhydride, a mixed anhydride or an acid halide (which can all be prepared in situ) is used, the condensation is carried out in an inert organic solvent, such as an ether (e.g. tetrahydrofuran or dioxan), a chlorinated hydrocarbon solvent (e.g. chloroform or methylene chloride), an amide (e.g. dimethylformamide or dimethylacetamide) or a ketone (e.g. acetone), or in a mixture of the above solvents, in the presence of an acid acceptor, such as an epoxide (e.g. propylene oxide) or an organic nitrogen-containing base, e.g. pyridine, N-methyl-morpholine or a trialkylamine (e.g. triethylamine), or in an aqueous-organic medium in the presence of an alkaline condensation agent, such as sodium bicarbonate, and the reaction is carried out at a temperature from $-40°$ to $+40°$ C., the resulting S-oxide is then reduced, if appropriate, and, if necessary, the protecting groups are replaced by hydrogen atoms.

If a reactive ester of general formula XXI is used, the reaction is generally carried out in the presence of a trialkylamine (e.g. triethylamine), in an organic solvent, such as dimethylformamide, at a temperature from 0° to 40° C., the resulting S-oxide is then reduced, if appropriate, and the protecting groups are replaced by hydrogen atoms.

The reduction of the oxide and the removal of the protecting groups are carried out in accordance with methods hereinbefore described.

The compounds of general formulae XI and XVI can be prepared by reacting an activated derivative of the acids $R'_4SO_3H$ and $R''_4COOH$, of the general formula:

| | |
|---|---|
| $(R'_4SO_2)_2O$ | XXII |
| $R'_4SO_2Hal$ | XXIII |
| $(R''_4CO)_2O$ | XXIV |
| $R''_4Co\ Hal$ | XXV |

(wherein $R'_4$ and $R''_4$ are as hereinbefore defined and Hal represents a halogen atom), with a compound (or a mixture of the isomers) of the general formula:

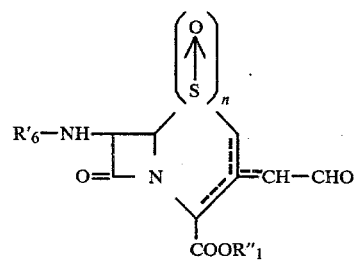 XXVI (wherein n is as hereinbefore defined and, when $n=0$, the compound is in the form of a bicyclooct-2-ene or -3-ene or a 3-oxoethylidenebicyclooctane, and when $n=1$, the compound is in the form of a bicyclooct-2-ene or a 3-oxoethylidenebicyclooctane, $R''_1$ is as hereinbefore defined for $R'_1$ except that $R''_1$ does not represent the hydrogen atom, and $R'_6$ represents a radical of the general formula:

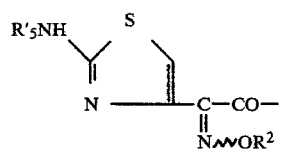 XXVII wherein $R^2$ is as hereinbefore defined, and $R'_5$ is as hereinbefore defined for $R_5$ except that $R'_5$ does not represent hydrogen, or $R'_6$ represents a radical $R_6$ as hereinbefore defined), followed, if necessary, by the reduction of the resulting sulphoxide and, if necessary, by the removal of protecting radicals on the amine group and the carboxylic acid group (if it is desired to obtain a compound of general formula XI in which $R'_1$ and/or $R_5$ represent hydrogen).

It is to be understood that, when $R'_6$ represents a radical of general formula XXVII in which $R^2$ represents hydrogen, it is necessary to protect the oxime. The oxime group may be protected and freed in accordance with the methods described above.

The reaction is generally carried out in the presence of a tertiary base of general formula XIV, e.g. triethylamine or N,N-dimethylaniline, in a chlorinated organic solvent (e.g. methylene chloride), in an ether (e.g. dioxan or tetrahydrofuran), in an amide (e.g. dimethylacetamide or dimethylformamide), in acetonitrile or N-methylpyrrolidone, or the reaction is carried out in a basic solvent, such as pyridine, at a temperature from $-78°$ C. to the reflux temperature of the reaction mixture.

It is not absolutely necessary for the intermediate of general formula XXVI to have been purified in order to carry out this reaction.

The removal of the protecting radicals on the amine group and the acid group may be carried out in accordance with the methods described above for the preparation of a compound of general formula IX.

The compounds of general formula XI can also be obtained by reacting an acid of general formula XX, in which the amine group has been protected, or by reacting one of its reactive derivatives, with a compound of the general formula:

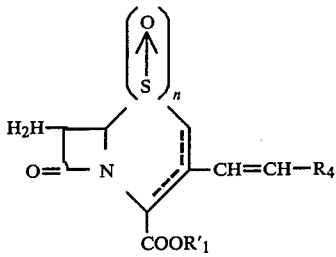

XXVIII (wherein R'₁, R₄ and n are as hereinbefore defined, and when n=0, the compound is in the form of a bicyclooct-2-ene or -3-ene, and when n=1, the compound is in the form of a bicyclooct-2-ene, and the substituent on the carbon atom in the 3-position of the bicyclooctene exhibits E/Z stereoisomerism) or, if appropriate, with a mixture of the isomers of this compound, followed, if necessary, by the reduction of the resulting oxide and then, if necessary, by the removal of protecting radicals.

The reaction is carried out under the conditions described above for the reaction of an acid of general formula XX with a 7-aminocephalosporin of general formula XIX.

If appropriate, the reduction of the oxide and also the removal of the protecting radicals can be carried out under the conditions described for the preparation of the compounds of general formula IX.

The compounds of general formula XXVIII can be obtained by removing the protecting radical R₆ from a compound of general formula XVI or, if appropriate, by simultaneously removing the radicals R₆ and R'₁ if it is desired to obtain a compound of the general formula XXVIII in which R'₁ is hydrogen.

The reaction is generally carried out under the conditions described above for the preparation of a compound of general formula XIX from a compound of general formula XV.

The compounds of general formula XXVI in which n is equal to 0 can be obtained by hydrolysing an enamine (or a mixture of isomeric enamines) of the general formula:

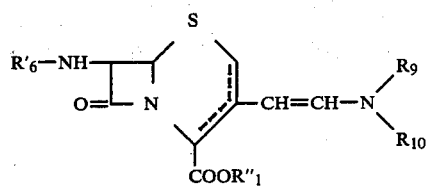

XXIX wherein R"₁ and R'₆ are as hereinbefore defined, the compound is in the form of a bicyclooct-2-ene or -3-ene and the substituent on the carbon atom in the 3-position of the bicyclooctene exhibits E/Z stereoisomerism, and R₉ and R₁₀, which are identical or different, represent alkyl radicals (which are optionally substituted by a hydroxy, alkoxy, amino, alkylamino or dialkylamino radical) or phenyl radicals, or form, together with the nitrogen atom to which they are attached, a saturated heterocyclic ring with 5 or 6 atoms in the ring, which may contain another hetero-atom selected from nitrogen, oxygen and sulphur and is optionally substituted by an alkyl radical on the second nitrogen atom.

Preferably, an enamine of general formula XXIX in which R₉ and R₁₀ each represent a methyl radical is hydrolysed.

The reaction is generally carried out in an organic acid (e.g. formic acid or acetic acid) or an inorganic acid (e.g. hydrochloric acid or sulphuric acid), in the presence or absence of a solvent, in an aqueous or organic medium, at a temperature from −20° C. to the reflux temperature of the reaction mixture. If the reaction is carried out in an organic medium, the hydrolysis is carried out by adding water to the reaction mixture and this is followed, if appropriate, by treatment with an inorganic base (e.g. an alkali metal bicarbonate) or an organic base (e.g. a tertiary amine or pyridine).

If the reaction is carried out in the presence of a solvent, it is not necessary for the solvent to be miscible with the acid aqueous phase. Contact is then produced by vigorous stirring.

Suitable solvents include a chlorinated hydrocarbon solvent, ethyl acetate, tetrahydrofuran, acetonitrile, dimethylformamide and alcohols. It is not absolutely necessary for the intermediate of the general formula XXIX to be purified before hydrolysis to prepare the compound of general formula XXVI.

The compounds of general formula XXVI in which n is equal to 1 can be obtained by oxidising the compounds of general formula XXVI in which n is equal to 0, by applying the method described in published German Patent Application 2,637,176.

The compounds of general formula XXIX in which R₉ and R₁₀ are as hereinbefore defined, other than those in which R₉ and R₁₀ represent alkyl substituted by hydroxy, amino or alkylamino, can be obtained by reacting a compound (optionally prepared in situ) of the general formula:

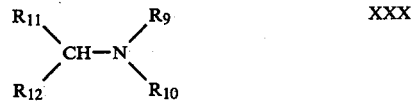

XXX (wherein R₉ and R₁₀ are as hereinbefore defined and R₁₁ and R₁₂, which are identical or different, either represent groups of the general formula:

—X₂R₁₃   XXXI wherein X₂ represents an oxygen atom and R₁₃ represents an alkyl or phenyl radical, or one of R₁₁ and R₁₂ represents a radical of general formula XXXI (in which X₂ represents an oxygen or sulphur atom and R₁₃ is alkyl or phenyl) and the other represents an amino radical of the general formula:

XXXII wherein R₁₄ and R₁₅ are as hereinbefore defined for R₉ and R₁₀, or R₁₁ and R₁₂ each represent a radical of general formula XXXII), with a cephalosporin derivative of the general formula:

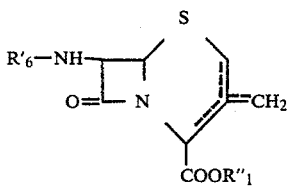

wherein R″₁ and R′₆ are as hereinbefore defined and the compound is in the form of a bicyclooct-2-ene or -3-ene or a 3-methylenebicyclooctane.

If a compound of general formula XXX in which the radical XXXII is different from —NR₉R₁₀ is chosen, it is preferable to choose this compound so that the amine HNR₁₄R₁₅ is more volatile than HNR₉R₁₀.

The reaction is generally carried out in an organic solvent, such as dimethylformamide, or in a mixture of solvents (e.g. dimethylformamide/tetrahydrofuran, dimethylformamide/dimethylacetamide, dimethylformamide/diethyl ether or dimethylformamide/dioxan), at a temperature from 20° C. to the reflux temperature of the reaction mixture.

It is to be understood that, when R′₆ represents a radical of general formula XXVII in which R² is a hydrogen atom, the oxime is preferably protected under the conditions described above.

The compounds of general formula XXIX in which R″₁ and R′₆ are as hereinbefore defined and R₉ and R₁₀ represent alkyl radicals substituted by hydroxy, amino or alkylamino can be obtained by trans-enamination from a compound of general formula XXIX in which R₉ and R₁₀ represent alkyl radicals, preferably methyl radicals.

The reaction is carried out by reacting an amine of the general formula:

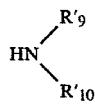

wherein R′₉ and R′₁₀, which are identical or different, represent alkyl radicals substituted by hydroxy, amino or alkylamino, with a compound of general formula XXIX, under the conditions described above for the reaction of a compound of general formula XXX with a derivative of general formula XXXIII.

The compounds of the general formula XXX can be prepared in accordance with the methods described by H. Bredereck et al, Chem. Ber. 101, 41 (1968), Chem. Ber. 101, 3,058 (1968) and Chem. Ber. 106, 3,725 (1973).

The cephalosporin derivatives of general formula XXXIII wherein R′₆ represents a radical of general formula XXVII can be prepared from a compound of the general formula:

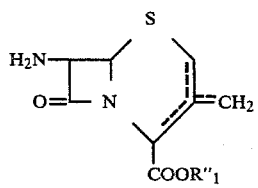

wherein R″₁ is as hereinbefore defined, by reaction with an acid of general formula XX, or a reactive derivative thereof, under the conditions described above for the preparation of a compound of general formula IX.

The cephalosporin derivatives of general formulae XXXIII and XXXV in which R″₁ represents a radical of general formula X can be obtained by esterifying the corresponding acids by known methods for preparing an ester from an acid without affecting the rest of the molecule.

In general, an alkali metal salt or a tertiary amine salt of the corresponding acid in which, if appropriate, the amine group and/or the oxime have been protected beforehand, is reacted with a compound of the general formula:

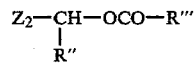

wherein R″ and R‴ are as hereinbefore defined and Z₂ represents a halogen atom, in an inert solvent, such as dimethylformamide, at a temperature from 0° to 30° C.

The compounds of general formula XXXVI can be prepared in accordance with the method described in published German Patent Application 2,350,230.

The introduction of the protecting groups R″₁ and R′₆ of the compound of general formula XXXIII (or XXXV in the case of R″₁) can be carried out on a 7-aminocephalosporin of the general formula:

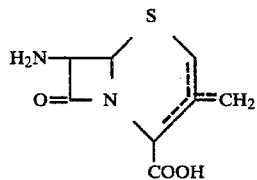

(wherein the position of the double bond is as hereinbefore defined for formulae XXXIII and XXXV) in accordance with known methods, i.e.

when R′₆ represents a formyl radical, according to J. C. Sheehan et al, J. Amer. Chem. Soc., 80, 1,156 (1958);

when R′₆ represents acetyl, chloroacetyl, trichloroacetyl, phenylacetyl, phenoxyacetyl or benzoyl, according to E. H. Flynn, Cephalosporins and Penicillins, Ac. Press (1972);

when R′₆ represents a t-butoxycarbonyl radical, according to L. Moroder et al, Hoppe Seyler's Z. Physiol. Chem., 357, 1,651 (1976);

when R′₆ represents 2,2,2-trichloro-1,1-dimethylethoxycarbonyl, according to J. Ugi et al., Angew. Chem. Int. Ed. Engl., 17(5), 361 (1978);

when R′₆ represents 2,2,2-trichloroethoxycarbonyl, 2-chloro-1,1-dimethylethoxycarbonyl, 2-cyano-1,1-dimethylethoxycarbonyl, 2-trimethylsilylethoxycarbonyl, benzyloxycarbonyl, p-methoxybenzyloxycarbonyl, 3,5-dimethoxybenzyloxycarbonyl, p-nitrobenzyloxycarbonyl or vinyloxycarbonyl, by reaction with a chloroformate in an aqueous-organic medium, in the presence of an alkali metal bicarbonate, or according to Belgian Pat. No. 788,885;

when R′₆ represents diphenylmethoxycarbonyl, by reaction with the corresponding azidoformate in an aqueous-organic medium, in the presence of an alkali metal bicarbonate;

when R′₆ represents 2-(biphenyl-4-yl)-isopropoxycarbonyl, by analogy with the method described in Helv. Chim. Acta, 51, 924 (1968);

when R'6 represents quinol-8-yl-oxycarbonyl or allyloxycarbonyl, by reaction with the corresponding carbonate in a basic aqueous-organic medium;

when R'6 represents a o-nitrophenylthio or p-nitrophenylthio, by analogy with the method described by L. Zervas et al, J. Amer. Chem. Soc., 85, 3,660 (1963);

when R'6NH- is replaced by dimethylaminomethyleneimino, by analogy with the method described by J. F. Fitt, J. Org. Chem., 42(15), 2,639 (1977);

when R'6NH- is replaced by 4-nitrobenzylideneimino or 3,4-dimethoxybenzylideneimino, in accordance with the method described by R. A. Sirestone, Tetrahedron Lett., 33, 2,915 (1977);

when R''1 represents methoxymethyl, according to S. Seki et al, Tetrahedron Lett., 33, 2,915 (1977);

when R''1 represents t-butyl, according to R. J. Stedman, J. Med. Chem., 9, 444 (1966);

when R''1 represents benzhydryl, according to published Dutch Patent Application 73/03,263 and when R''1 represents p-nitrobenzyl or p-methoxybenzyl, according to R. R. Chauvette et al, J. Org. Chem., 38(17), 2,994 (1973).

The compounds according to the invention can also be used to prepare cephalosporins of general formula IX, by proceeding in the following manner: A thioloester of the general formula:

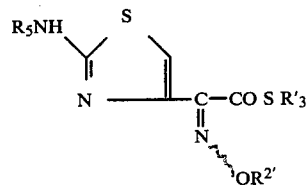

(wherein R5 is as hereinbefore defined, R2' is as hereinbefore defined for R2 or represents a protecting radical selected from trityl, tetrahydropyranyl and 2-methoxyprop-2-yl and R'3 is as hereinbefore defined for R3, it being understood that the amino or alkylamino groups contained in this radical are necessarily protected and that the hydroxy groups are free or protected) is prepared by reacting a thiol of general formula I or an alkali metal or alkaline earth metal salt thereof with an acid, or a reactive derivative of the acid, of the general formula:

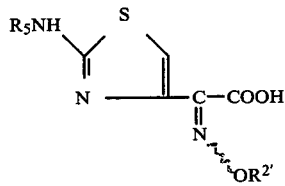

wherein R5 and R2' are as hereinbefore defined, except that R5 and R2' do not represent a hydrogen atom, followed by the removal of the protecting radical R5 of the aminothiazole, if it is desired to obtain a thioloester of general formula XXXVIII in which R5 is a hydrogen atom, and, if appropriate, of the other protecting radicals.

If it is desired to obtain a thioloester in which R2' is a hydrogen atom, the protection of the oxime can be carried out by any known method which does not affect the rest of the molecule, in particular by means of the trityl radical, which can be removed after the reaction.

If it is desired to obtain a compound in which R'3 contains a hydroxy radical, it is preferable to protect this group beforehand, e.g. by means of a trityl radical.

It is advantageous not to remove these protecting groups until after the thiloesters have been used to prepare the compounds of general formula IX. Suitable conditions for the reaction of a compound of general formula I and an acid of general formula XXa or a reactive derivative thereof are as follows:

(a) If the compound of general formula XXa is used in the form of the acid, the condensation is generally carried out in an organic solvent, such as dimethylformamide, acetonitrile, tetrahydrofuran, methylene chloride, chloroform or ethyl acetate, in the presence of a condensation agent, such as a carbodiimide (e.g. dicyclohexylcarbodiimide), N,N'-carbonyldiimidazole or 2-ethoxy-1-ethoxycarbonyl-1,2-dihydroquinoline, at a temperature from −20° to 40° C., and the protecting groups are then removed, if appropriate.

(b) If a reactive derivative of the acid of general formula XXa is used, it is possible to use the anhydride, a mixed anhydride, an acid halide or a reactive ester of the general formula:

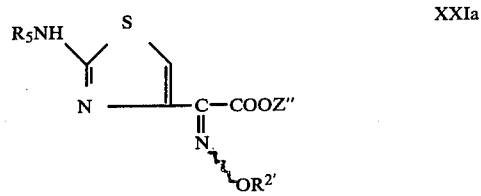

wherein R2' and R5 are as hereinbefore defined and Z'' represents a radical such as succinimido, benzotriazol-1-yl, 4-nitrophenyl, 2,4-dinitrophenyl, pentachlorophenyl or phthalimido.

(c) If it is desired to obtain a compound of general formula XXXVIII in which R5 is a hydrogen atom, it is also possible to use an acid halide, e.g. the acid chloride, the hydrochloride of the chloride of the acid of the general formula XX being reacted with the thiol of general formula I or with one of its salts.

If the anhydride, a mixed anhydride or an acid halide (which can all be prepared in situ) is used, the condensation is carried out in an inert organic solvent, such as an ether (e.g. tetrahydrofuran or dioxan), a chlorinated hydrocarbon solvent (e.g. chloroform or methylene chloride), an amide (e.g. dimethylformamide or dimethylacetamide), or a ketone (e.g. acetone), or also in mixtures of the above solvents, in the presence of an acid acceptor, such as an epoxide (e.g. propylene oxide) or a nitrogen-containing organic base, e.g. pyridine, N-methylmorpholine or a trialkylamine (e.g. triethylamine), or in an aqueous-organic medium in the presence of an alkaline condensation agent, such as sodium bicarbonate, and the reaction is carried out at a temperature from −40° to +40° C., and the protecting group or groups are then removed, if appropriate.

If a reactive ester of general formula XXIa is used, the reaction is generally carried out in the presence of a trialkylamine (e.g. triethylamine), in an organic solvent, such as dimethylformamide, at a temperature from 0° to 60° C., and the protecting group or groups are then removed, if appropriate.

By way of example, the various protected radicals can be freed under the following conditions:

if it is desired to obtain a compound of general formula XXXVIII in which $R_5$ is hydrogen, a t-butoxycarbonyl radical protecting the aminothiazole is removed by treatment in an anhydrous acid medium. In this case, the product is obtained either in the form of a salt or in the form of a solvate with the acid employed. Preferably, trifluoroacetic acid is used, the reaction being carried out at from 0° to 20° C. A benzyl radical protecting the aminothiazole can also be removed by catalytic hydrogenation;

if it is desired to obtain a compound of general formula XXXVIII in which the radical $R'_3$ comprises a hydroxy group and/or in which $R^{2'}$ is a hydrogen atom, the trityl group or groups are removed by acid hydrolysis by means of anhydrous trifluoroacetic acid. The removal is carried out before, simultaneously with or after the removal of the protecting radical on the aminothiazole.

A product of general formula IX, as hereinbefore defined, is thus prepared by reacting the thioloester of general formula XXXVIII with a 7-aminocephalosporin of general formula XXVIII, and then by reducing the resulting sulphoxide (if the sulphoxide of the product of general formula XXVIII has been used) and by removing the protecting radicals.

It is to be understood that the thioloesters in the syn or anti form, or mixtures thereof, lead to the products of general formula IX in the syn or anti form, or mixtures thereof, respectively.

It is also to be understood that the radicals $R_3'$ which comprise a group capable of interfering with the reaction are protected beforehand. The same applies to the oxime if $R^{2'}$ represents the hydrogen atom.

Likewise, as for the processes described above, if R contains a hydroxy or sulphonyl substituent, it is preferred to use a product of general formula XXVIII in which $n=0$.

The protection and the removal of the protecting radicals are carried out under conditions hereinbefore described.

The reaction of the thioloester of general formula XXXVIII with the 7-aminocephalosporin of general formula XXVIII is generally carried out in the presence of an acid acceptor, such as an organic base, and more particularly in the presence of a pyridine or a tertiary organic base of the general formula XIV, in particular triethylamine, N,N-diisopropyl-N-ethylamine, diethylphenylamine or N-methylmorpholine.

The reaction is advantageously carried out in an organic solvent, such as an amide (e.g. dimethylformamide or dimethylacetamide), an ether (e.g. tetrahydrofuran or dioxan), a chlorinated hydrocarbon solvent (e.g. chloroform or methylene chloride), a ketone (e.g. acetone) or a nitrile (e.g. acetonitrile), or alternatively in a mixture of these solvents. The reaction can also be carried out in the presence of an alkali metal bicarbonate, in one of the abovementioned solvents, if appropriate in the presence of water.

The reaction is carried out at a temperature from $-20°$ C. to the reflux temperature of the reaction mixture. If appropriate, it is carried out under a nitrogen atmosphere.

The reduction of the S-oxide and the removal of the protecting radicals are carried out under the conditions described above.

The acids of general formula XX in which $R^2$ is hydrogen, alkyl or trityl can be prepared in accordance with the method described in Belgian Pat. No. 850,662.

The acids of general formula XX in which $R^2$ is a vinyl radical can be prepared in accordance with the method described in Belgian Pat. No. 869,079.

The acids of the general formula XX in which $R^2$ is a cyanomethyl radical can be prepared in accordance with the method described in published German Patent Application 2,812,625.

The acids of general formula XX in which $R^2$ is a protecting radical can be prepared by protecting the oxime of this acid, in which $R^2$ is hydrogen, by any known method which does not affect the rest of the molecule. The protection is preferably carried out by means of trityl, tetrahydropyranyl or 2-methoxyprop-2-yl groups.

The compounds of general formulae XI, XV, XVI, XIX or XXVIII in which n is equal to 1 can be obtained respectively by oxidising the corresponding compounds of the general formulae XI, XV, XVI, XIX or XXVIII in which n is equal to 0, by applying the method described in published German Patent Application 2,637,176.

The isomers of the compounds of general formulae IX, XI, XV, XVI, XIX, XXVI, XXVIII, XXIX or XXXVIII can be separated by chromatography or crystallisation.

The compounds of general formula I and the compounds of general formula IX can be purified by physical methods, such as crystallisation or chromatography.

The compounds of general formula I can be converted to alkali metal or alkaline earth metal salts by known methods for the preparation of thiolates, which do not affect the rest of the molecule.

The compounds of general formula IX can be converted to addition salts with acids. In accordance with the processes described above, they can be obtained in the form of the trifluoroacetate, a solvate with formic acid or with water, the para-toluenesulphonate or the methanesulphonate. The compounds of general formula IX, in which $R_3$ is as hereinbefore defined, which are obtained in the form of these salts can be freed and converted to salts of other acids by known methods.

The acids of general formula IX can also be converted to metal salts or to addition salts with nitrogen-containing bases. These salts can be obtained by reacting a metal base (e.g. an alkali metal base or alkaline earth metal base), ammonia or an amine with an acid of general formula IX, in a suitable solvent, such as an alcohol, an ether or water, or by an exchange reaction with a salt of an organic acid. The salt formed precipitates, after concentration, if necessary, of its solution, and is separated off by filtration or decantation. It can also be isolated by lyophilisation of its solution.

The cephalosporin derivatives of general formula IX and their pharmaceutically acceptable salts exhibit particularly valuable anti-bacterial properties. They show a remarkable in vitro and in vivo activity against Gram-positive and Gram-negative germs.

In vitro, the compounds of general formula IX are active at a concentration of between 0.5 and 15 $\mu$g/cc against staphylococcus strains which are sensitive to penicillin G (*Staphylococcus aureus* Smith), at a concentration of between 1 and 30 $\mu$g/cc against staphylococcus strains which are resistant to penicillin G (*Staphylococcus aureus* MB 9), at a concentration of between 0.001 and 1 $\mu$g/cc against *Escherichia coli*, Monod strain, and at a concentration of between 0.06 and 30 μg/cc against *Klebsiella pneumoniae.* Furthermore, some of these products have shown themselves to be active at a concentration of between 0.01 and 30 μg/cc against *Proteus morganii* and at a concentration of between 0.1 and 30 μg/cc against *Enterobacter aerogenes.*

In vivo, the compounds of general formula IX are active at a dose of between 0.2 and 15 mg/kg per day, administered subcutaneously, against experimental infections caused in mice by *Staphylococcus aureus* Smith (sensitive to penicillin G), and at doses of between 0.001 and 10 mg/kg per day, administered subcutaneously, against those caused by *Escherichia coli* (Monod strain).

Furthermore, the $LD_{50}$ of the compounds of the general formula IX is between 1.5 g/kg and doses of more than 2.5 g/kg, administered subcutaneously to mice.

Of particular value are the compounds of general formula I in which: A represents a 2-hydroxy-1-oxoethan-1-yl-2-ylidene radical and R represents a protected 2,3-dihydroxypropyl or protected 1,3-dihydroxyprop-2-yl radical, an alkyl radical containing 2 to 4 carbon atoms, substituted by an alkylsulphonylamino radical, an acylamino radical (in which the acyl moiety is substituted by amino), or an alkoxycarbonylamino or alkylureido radical, or represents a phenylalkyl or alkylthioalkyl radical or a radical of the formula IIIb or IIIc, or A represents a nitrogen atom and R represents optionally protected 1,3-dihydroxyprop-2-yl or a radical of general formula IIIc.

Particularly preferred compounds of general formula I are those in which A represents a 2-hydroxy-1-oxoethan-1-yl-2-ylidene radical and R represents a protected 2,3-dihydroxypropyl radical, an alkyl radical containing 2 to 4 carbon atoms substituted by an alkoxycarbonylamino radical, or represents a phenylalkyl or alkylthioalkyl radical or a radical of the formula IIIb or IIIc, or A represents a nitrogen atom and R represents an optionally protected 1,3-dihydroxyprop-2-yl radical or a radical of general formula IIIc.

The following Examples illustrate the present invention.

EXAMPLE 1

4-Benzylthiosemicarbazide (9.06 g), prepared according to W. BAIRD et al., J. Chem. Soc., 2,527 (1927), is added to a solution, at 20° C., of sodium (1.15 g) in methanol (50 cc), and diethyl oxalate (6.76 cc) is then added. The mixture is heated under reflux for 2 hours and cooled at 4° C. for 3 hours and the precipitate is filtered off. The sodium salt thus obtained is dissolved in water (50 cc) and the solution is acidified to pH=2 by adding 1 N hydrochloric acid, whilst cooling at 4° C. After one hour, the product is filtered off and dried and 4-benzyl-5,6-dioxo-3-thioxo-perhydro-1,2,4-triazine (9.2 g) is collected.

Infra-red spectrum (KBr), characteristic bands in $cm^{-1}$: 3,440, 3,320, 1,680, 1,625, 1,495, 1,450, 1,350, 730 and 695.

EXAMPLE 2

4-(2-Methylthioethyl)-thiosemicarbazide (13.6 g) is added to a solution of sodium (1.83 g) in methanol (80 cc), and diethyl oxalate (10.8 cc) is then added dropwise in the course of 15 minutes. The mixture is heated under reflux for 3 hours and left to cool and diethyl ether (1 liter) is added, whilst stirring. The precipitate is filtered off. The resulting yellow solid is dissolved in water (100 cc) and the pH of the solution is adjusted to 2 by adding 1 N hydrochloric acid, whilst cooling in an ice bath.

After filtration and drying, a white solid (3 g) is collected, which is purified by 2 successive crystallisations from boiling water (50 cc). This yields 5,6-dioxo-4-(2-methylthioethyl)-3-thioxo-perhydro-1,2,4-triazine (2.4 g).

Infra-red spectrum (KBr), characteristic bands in $cm^{-1}$: 3,550, 3,490, 3,280, 3,220 and 1,690.

4-(2-Methylthioethyl)-thiosemicarbazide can be prepared by adding hydrazine hydrate (6.8 cc) to a solution of methyl N-(2-methylthioethyl)-dithiocarbamate (26 g) in ethanol (500 cc) and heating under reflux for 3 hours. After concentration to dryness at 20° C. under 20 mm Hg (2.7 kPa), the resulting oil is triturated with diethyl ether (100 cc). The crystals formed are filtered off and dried. The thiosemicarbazide (18.16 g), m.p.=70° C., is collected.

Infra-red spectrum (KBr), characteristic bands in $cm^{-1}$: 3,320, 3,200, 3,160, 1,635, 1,550 and 1,260.

EXAMPLE 3

A solution of sodium methylate is prepared by dissolving sodium (4.15 g) in methanol (140 cc), 4-(2,2-dimethoxyethyl)-thiosemicarbazide (32.3 g) is added and ethyl oxalate (26.3 g) is added. The mixture is heated under reflux for 4 hours, whilst stirring, and left to cool. After one night, the resulting suspension is filtered and the precipitate is washed with ether (3×25 cc). The solid is dissolved in water (40 cc) and, after cooling to about 4° C., the solution is acidified to pH 3 with 4 N hydrochloric acid and left at 4° C. for 30 minutes. After filtration and drying, 4-(2,2-dimethoxyethyl)-5,6-dioxo-3-thioxo-perhydro-1,2,4-triazine (12 g) is collected in the form of a white solid. Instantaneous m.p. (Kofler)=172° C. (decomposition).

Infra-red spectrum (KBr), characteristic bands in $cm^{-1}$: 3,280, 3,250, 1,695, 1,380, 1,130 and 1,050.

Proton NMR spectrum (80 MHz, $d_6$-DMSO, δ in ppm, J in Hz): 3.30 (s, 6H, -OCH$_3$); 4.38 (d, J=5.5, 2H, >NCH$_2$-); and 4.94 (t, J=5.5, 1H, -C$\underline{H}$(OCH$_3$)$_2$).

2,2-Dimethoxyethyl isothiocyanate (37.7 g) is added in the course of 1 hour, whilst stirring, at a temperature between 5° and 9° C., to a solution of hydrazine hydrate (14.35 g) in ethanol (40 cc). After 12 hours at 4° C., the mixture is concentrated to dryness at 20° C. under reduced pressure (20 mm Hg; 2.7 kPa). The resulting yellow syrup crystallises after initiation. The solid is dissolved in hot methanol (50 cc), the solution is filtered and the filtrate is diluted with diethyl ether (200 cc). After about ten hours at 4° C., the product is filtered off and 4-(2,2-dimethoxyethyl)-thiosemicarbazide (32.3 g) is collected in the form of a white solid.

Instantaneous m.p. (Kofler)=69° C.

EXAMPLE 4

4-(2,2-Diethoxyethyl)-thiosemicarbazide (18.6 g) and diethyl oxalate (13.15 g) are added successively to a solution of sodium (2.07 g) in dry methanol (70 cc) and the mixture is heated under reflux for 4 hours, under nitrogen. The cooled mixture is diluted with water (300 cc) and ethyl acetate (150 cc) and then acidified to pH=2 with concentrated hydrochloric acid, whilst cooling at 4° C. The organic phase is decanted, the aqueous phase is extracted with ethyl acetate (3×100 cc), the organic phase is washed with a saturated solution of sodium chloride (3×100 cc), dried over sodium sulphate and filtered and the filtrate is concentrated to dryness at 20° C. under 20 mm Hg (2.7 kPa). A thick yellow oil (22.6 g), consisting mainly of 4-(2,2-diethoxyethyl)-5,6-dioxo-3-thioxo-perhydro-1,2,4-triazine, is collected.

Proton NMR spectrum (80 MHz, d6-DMSO, δ in ppm, J in Hz): 1.1 to 1.3 (m, 6H, CH3-), 3.36 to 3.6 (m, 4H, -OCH2-), 4.4 (d, J=6, 2H, -CH2CH<), 5.1 (t, J=6, 1H, -CH<).

4-(2,2-Diethoxyethyl)-thiosemicarbazide can be prepared in the following manner:

Hydrazine hydrate (27.3 cc) is added in the course of 1 hour, at 4° C., to a solution of 2,2-diethoxyethyl isothiocyanate (94 g) in ethanol (150 cc). The mixture is stirred for a further 20 minutes at 4° C. and the mixture is filtered; this yields the desired product (86 g), which is a white solid, m.p.=96° C.

EXAMPLE 5

A solution of sodium (1.12 g) in anhydrous methanol (50 cc) is prepared, 4-(2,2-dimethyldioxolan-4-yl-methyl)-thiosemicarbazide (10 g) is added at 25° C., under nitrogen and whilst stirring, diethyl oxalate (6.6 cc) is then added dropwise in the course of 10 minutes and the mixture is heated under reflux for 2 hours. It is left to cool to 20° C., diluted with diethyl ether (1 liter) and filtered and, after drying, a white solid (3.7 g) is collected. The product is taken up in methylene chloride (200 cc) and the mixture is stirred in the presence of 1 N hydrochloric acid (10 cc). The organic phase is decanted, washed with water saturated with sodium chloride (2×50 cc), dried over sodium sulphate and concentrated to dryness at 20° C. under 20 mm Hg (2.7 kPa). The residual oil is taken up in methylene chloride (50 cc), crystallisation is initiated by scratching and the mixture is left at 4° C. for 3 hours. After filtration and drying, 4-(2,2-dimethyldioxolan-4-yl-methyl)-5,6-dioxo-3-thioxo-perhydro-1,2,4-triazine (1.5 g) is collected in the form of white crystals.

Infra-red spectrum (KBr), characteristic bands (cm⁻¹): 3,600–3,100, 1,680, 1,575, 1,535, 1,210 and 1,060.

Proton NMR spectrum (80 MHz, d6-DMSO, δ in ppm, J in Hz): 1.30 and 1.42 (2s, 6H, >C(CH3)2); 3.95 (m, 2H, -CH2O-); and 4.50 (m, 3H,

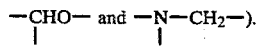

4-(2,2-Dimethyldioxolan-4-yl-methyl)-thiosemicarbazide can be prepared in the following manner:

A mixture of methyl N-(2,2-dimethyldioxolan-4-yl-methyl)-dithiocarbamate (23.6 g), prepared according to U.S. Pat. No. 4,064,242, absolute ethanol (500 cc) and hydrazine hydrate (5.6 g) is heated under reflux for 2 hours 30 minutes. It is concentrated to dryness at 20° C. under 20 mm Hg (2.7 kPa) and the residue is taken up in diethyl ether (100 cc). After filtration and drying, 4-(2,2-dimethyldioxolan-4-yl-methyl)-thiosemicarbazide (15.2 g) is collected in the form of a cream-coloured solid melting at 145° C.

Infra-red spectrum (KBr), characteristic bands (cm⁻¹): 3,340, 3,200, 1,630, 1,555, 1,510, 1,380, 1,370, 1,240, 1,210 and 1,060.

Proton NMR spectrum (80 MHz, CDCl3, δ in ppm, J in Hz): 1.38 and 1.48 (2s, 6H, >C(CH3)2); 3.72 (dd, J=5 and 6, 2H,

3.90 (s, 2H, -NH2); 4.10 (dd, J=6 and 7, 2H, -CH2O-); 4.38 (m, 1H, >CHO-); 7.78 (t, J=5, 1H, -CH2NH-); and 7.98 (s, 1H,

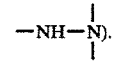

EXAMPLE 6

4-(2-t-Butoxycarbonylaminoethyl)-thiosemicarbazide (9.37 g) is added, at 20° C., to a solution of sodium (0.92 g) in methanol (40 cc), and diethyl oxalate (5.4 g) is added dropwise in the course of 10 minutes. The mixture is heated under reflux for 3 hours. It is left to cool, water (100 cc) is added, concentrated hydrochloric acid (3 cc) is added dropwise, the mixture is extracted with ethyl acetate (2×100 cc), the extract is washed with a saturated solution of sodium chloride (2×50 cc), dried over sodium sulphate and filtered and the filtrate is concentrated to dryness at 20° C. under 20 mm Hg (2.7 kPa). The residue is taken up in methylene chloride (65 cc), crystallisation is initiated, the mixture is left for 2 hours at 20° C. and filtered and white crystals (4.59 g), melting at 160° C., of 4-(2-t-butoxycarbonylaminoethyl)-5,6-dioxo-3-thioxo-perhydro-1,2,4-triazine are collected.

Infra-red spectrum (KBr), characteristic bands (cm⁻¹): 3,380, 3,150, 1,685, 1,640, 1,545 and 1,370.

Proton NMR spectrum (80 MHz, DMSO d6, δ in ppm, J in Hz): 1.45 (s, 9H, -C(CH3)3); 3.32 (q, J=5, 2H, -CH2CH2NH-); 4.38 (t, J=5, 2H, -CH2-CH2-N-); 6.72 (d, J=5, 1H, .CH2CH2NH-); and 12.3 (s broad, 1H, -NH- triazine).

4-(2-t-Butoxycarbonylaminoethyl)-thiosemicarbazide can be prepared in the following manner:

A mixture of methyl N-(2-t-butoxycarbonylaminoethyl)-dithiocarbamate (22.53 ), ethanol (90 cc) and hydrazine hydrate (4.4 cc) is heated under reflux for 1 hour 30 minutes. The solution is concentrated to dryness at 30° C. under 20 mm Hg (2.7 kPa) and the residue is triturated in the presence of diethyl ether (100 cc). Crystallisation starts in the course of 5 minutes. The mixture is left for 1 hour at 20° C. and the product is filtered off and dried. This yields pinkish white crystals (11.3 g), melting at 85° C., of 4-(2-t-butoxycarbonylaminoethyl)-thiosemicarbazide.

Infra-red spectrum (CHBr3), characteristic bands (cm⁻¹): 3,450, 3,350, 1,700, 1,620, 1,545, 1,510, 1,390, 1,370, 1,250, 1,225 and 1,160.

Proton NMR spectrum (80 MHz, CDCl3, δ in ppm, J in Hz): 1.48 (s, 9H, -C(CH3)3); 3.45 and 3.80 (2t, J=5, 4H, -CH2CH2-).

Triethylamine (15.5 cc) is added to a solution of 2-t-butoxycarbonylaminoethylamine (17.62 g) in 95% strength ethanol (110 cc), and carbon disulphide (6.65 cc) is added dropwise in the course of 10 minutes, whilst keeping the temperature between 20° C. and 25° C. The mixture is stirred for 1 hour 30 minutes at 22° C. Methyl iodide (6.85 cc) is then added and the mixture is stirred for 1 hour 30 minutes at 22° C. It is concentrated to dryness at 20° C. under 20 mm Hg (2.7 kPa), the residue is taken up in ethyl acetate (200 cc), the mixture is washed with water (3×100 cc), dried over sodium sulphate and filtered and the filtrate is concentrated to dryness at 20° C. under 20 mm Hg (2.7 kPa). Methyl N-(2-t-butoxycarbonylaminoethyl)-dithiocarbamate (23.2 g) is collected in the form of a yellow oil.

Infra-red spectrum (CHBr$_3$), characteristic bands (cm$^{-1}$): 3,440, 3,370, 1,700, 1,505, 1,430, 1,380, 1,370 and 945.

Proton NMR spectrum (60 MHz, CDCl$_3$, δ in ppm, J in Hz): 1.50 (s, 9H, -C(CH$_3$)$_3$); 2.65 (s, 3H, -CH$_3$); and 3.50 and 3.80 (2t, J=5, 4H, -CH$_2$-CH$_2$-).

2-t-Butoxycarbonylaminoethylamine is prepared by the hydrazinolysis of N-t-butoxycarbonyl-phthalimidoethylamine:

Hydrazine hydrate (10.8 cc) is added to a suspension of N-t-butoxycarbonyl-2-phthalimidoethylamine (53.7 g) in ethanol (540 cc) and the mixture is heated under reflux for 25 minutes. The mixture is cooled to 0° C. and filtered. The filtrate is concentrated to dryness under reduced pressure (20 mm Hg; 2.7 kPa). This yields 2-(N-t-butoxycarbonylamino)-ethylamine (19.6 g) in the form of a yellow oil.

Infra-red spectrum (CHCl$_3$), characteristic bands (cm$^{-1}$): 3,460, 3,380, 3,320, 1,700, 1,585, 1,500, 1,390, 1,370, 1,160 and 490.

Proton NMR spectrum (60 MHz, CDCl$_3$, δ in ppm, J in Hz): 1.48 (s, 9H, -C(CH$_3$)$_3$); 2.20 (s broad, 2H, -NH$_2$); 2.80 (t, J=5, 2H, H$_2$N-CH$_2$-CH$_2$-); 3.18 (t, J=5, 2H, H$_2$NCH$_2$CH$_2$-); and 5.50 (s broad, 1H, -NHCO-).

EXAMPLE 7

2,2-Dimethyl-5-isothiocyanato-1,3-dioxane (7 g) in dimethylformamide (15 cc) is added dropwise to sodium nitride (3.43 g) in dimethylformamide (80 cc) at 50° C. The mixture is then heated to 80° C. A solid is filtered off and the filtrate is concentrated to dryness under reduced pressure (0.5 mm Hg; 0.07 kPa) at 40° C. The residue is taken up in ethyl ether (100 cc), and the sodium salt of 1-(2,2-dimethyl-1,3-dioxan-5-yl)-5-mercaptotetrazole (8.5 g) is isolated by filtration.

Infra-red spectrum (KBr), characteristic bands (cm$^{-1}$): 1,390, 1,360, 1,280, 1,115, 1,060 and 825.

2,2-Dimethyl-5-isothiocyanato-1,3-dioxane can be prepared in the following manner.

Dicyclohexylcarbodiimide (5.3 g) is added to a solution of 2,2-dimethyl-5-amino-1,3-dioxane (3.4 g) in tetrahydrofuran (100 cc). After dissolution, the mixture is cooled to −10° C. and carbon disulphide (12.9 g) is added, whilst keeping the temperature at −10° C. The mixture is left to stand overnight, whilst allowing the temperature to return to about 20° C.

The mixture is concentrated to dryness under reduced pressure (20 mm Hg; 2.7 kPa), the residue is taken up in ethyl ether (50 cc), whilst stirring, a solid is filtered off and washed with ethyl ether (20 cc), and the ether solutions are concentrated to dryness under reduced pressure (20 mm Hg; 2.7 kPa). This yields 2,2-dimethyl-5-isothiocyanato-1,3-dioxane (4.1 g) in the form of a viscous orange oil.

Infra-red spectrum (CHCl$_3$): -N=C=S 2,100 cm$^{-1}$.

2,2-Dimethyl-5-amino-1,3-dioxane can be prepared in the following manner:

2,2-Dimethyl-5-nitro-1,3-dioxane (22 g) dissolved in tetrahydrofuran (200 cc) is reduced with hydrogen at a temperature of the order of 20° C., under 5.10$^3$ kPa, in the presence of Raney nickel (15 g). After the catalyst has been filtered off, the mixture is concentrated to dryness under reduced pressure (20 mm Hg; 2.7 kPa). This yields 2,2-dimethyl-5-amino-1,3-dioxane (16.3 g) in the form of a pale yellow oil.

Infra-red spectrum (CHCl$_3$), characteristic bands (cm$^{-1}$): 3,380, 1,585, 1,380, 1,375, 1,080, 1,055 and 940.

2,2-Dimethyl-5-nitro-1,3-dioxane can be prepared in accordance with the method described by G. B. LINDEN and M. H. GOLD, J. Org. Chem., 21, 1,175 (1956).

EXAMPLE 8

4 N hydrochloric acid (50 cc) is added to the sodium salt of 1-(2,2-dimethyl-1,3-dioxan-5-yl)-5-mercaptotetrazole (as obtained in accordance with Example 7) (22 g) in water (100 cc) and the mixture is heated for 30 minutes at 80° C. 4 N sodium hydroxide solution (25 cc) is added and the mixture is concentrated to dryness under reduced pressure (20 mm Hg; 2.7 kPa). The residue is taken up in boiling acetonitrile (2×100 cc), an insoluble material is filtered off, the acetonitrile is evaporated off under reduced pressure (20 mm Hg; 2.7 kPa) and the residue is taken up in ethyl ether (100 cc). 1-(1,3-Dihydroxyprop-2-yl)-5-mercaptotetrazole (11 g), melting at 138° C., is isolated by filtration.

EXAMPLE 9

A solution of sodium (0.46 g) in methanol (60 cc) is prepared, 4-(3,3-diethoxy-2-hydroxypropyl)-thiosemicarbazide (4.74 g) and ethyl oxalate (2.73 cc) are added and the mixture is then heated under reflux for 5 hours under nitrogen, whilst stirring. The reaction mixture is concentrated to 20 cc at 20° C. under 20 mm Hg (2.7 kPa) and filtered, the white solid is washed with methanol (3 cc) and diethyl ether (2×5 cc) and dried at 20° C. under 0.05 mm Hg (0.007 kPa) and the sodium salt of 4-(3,3-diethoxy-2-hydroxypropyl)-5,6-dioxo-3-thioxo-perhydro-1,2,4-triazine (3.2 g) is collected in the form of a white powder.

Infra-red spectrum (KBr), characteristic bands (cm$^{-1}$): 3,190, 1,685, 1,595, 1,560, 1,095 and 1,065.

The thiosemicarbazide can be prepared in the following manner:

A solution of methyl N-(3,3-diethoxy-2-hydroxypropyl)-dithiocarbamate (15.8 g) and hydrazine hydrate (3.03 cc) in ethanol (60 cc) is heated under reflux for 1 hour 30 minutes and then left to stand for 12 hours at 20° C. and the solvent is driven off in vacuo at 20° C. under 20 mm Hg (2.7 kPa). The residue is dissolved in ethyl acetate (25 cc) and the solution is chromatographed on a column of Merck silica gel (0.06–0.2) (100 g) (diameter of the column: 3 cm, height: 41 cm); elution is carried out with ethyl acetate (1 liter), 100 cc fractions being collected. Fractions 3 to 8 are evaporated to dryness at 20° C. under 20 mm Hg (2.7 kPa), the residue is taken up in diethyl ether (35 cc) and crystallisation is initiated, the mixture is left for 30 minutes at 5° C., the product is filtered off and dried and 4-(3,3-diethoxy-2-hydroxypropyl)-thiosemicarbazide (6.1 g) is collected in the form of white crystals melting at 83° C.

Infra-red spectrum (CHBr$_3$), characteristic bands (cm$^{-1}$): 3,560, 3,340, 1,615, 1,540, 1,085 and 1,055.

Triethylamine (9.11 cc) is added to a solution, at 20° C., of (3,3-diethoxy-2-hydroxypropyl)-hydrazine (prepared according to U.S. Pat. No. 2,875,248) (10.6 g) in 95% strength (w/w) ethanol (50 cc), and carbon disulphide (3.92 cc) is then added dropwise. After stirring for 1 hour 15 minutes, methyl iodide (4.04 cc) is added; the temperature rises to 35° C.; the mixture is stirred for 2 hours and evaporated to dryness at 20° C. under 20 mm Hg (2.7 kPa). The residue is taken up in ethyl acetate (240 cc), the mixture is washed with a 0.1 M solution of sodium thiosulphate (2×100 cc) and water (100 cc), dried over sodium sulphate and filtered and the filtrate is concentrated to dryness at 20° C. under 20 mm Hg (2.7 kPa). Methyl N-(3,3-diethoxy-2-hydroxypropyl)-dithiocarbamate (15.9 g) is collected in the form of a yellow oil.

Infra-red spectrum (CHBr$_3$), characteristic bands (cm$^{-1}$): 3,560, 3,360, 1,495, 1,370, 1,060 and 940.

The products of the general formula (I) can be used to prepare the products of the general formula (IX) by following the procedures given in the examples below.

REFERENCE EXAMPLE 1

The product of Example 1 can be used as follows:

A mixture of the E form of the syn isomer of 2-benzhydryloxycarbonyl-7-[2-methoxyimino-2-(2-tritylaminothiazol-4-yl)-acetamido]-8-oxo-3-(2-tosyloxyvinyl)-5-thia-1-azabicyclo[4.2.0]oct-2-ene-5-oxide (10.04 g), dimethylformamide (200 cc), 4-benzyl-5,6-dioxo-3-thioxoperhydro-1,2,4-triazine (2.82 g) and diisopropylethylamine (2.1 cc) is stirred at 60° C. for 3 hours. It is poured into ethyl acetate (500 cc), the mixture is washed with water (2×250 cc) and a saturated solution of sodium chloride (2×200 cc), dried over sodium sulphate and filtered and the filtrate is concentrated to dryness at 20° C. under 20 mm Hg (2.7 kPa). The residue is dissolved in a mixture of cyclohexane/ethyl acetate (20/80 by volume) (30 cc) and this solution is chromatographed on a column of Merck silica gel (0.04–0.06) (200 g) (diameter of the column: 8 cm, height: 30 cm). Elution is carried out with a mixture of cyclohexane/ethyl acetate (20/80 by volume) (2 liters), a mixture of cyclohexane/ethyl acetate (10/90 by volume) (2 liters) and ethyl acetate (2 liters) under a pressure of 40 kPa, 100 cc fractions being collected. Fractions 45 to 60 are evaporated to dryness at 20° C. under 20 mm Hg (2.7 kPa) and this yields the E form of the syn isomer of 2-benzhydryloxycarbonyl-3-[2-(4-benzyl-5,6-dioxo-1,4,5,6-tetrahydro-1,2,4-triazin-3-yl)-thiovinyl]-7-[2-methoxyimino-2-(2-tritylaminothiazol-4-yl)-acetamido]-8-oxo-5-thia-1-azabicyclo[4.2.0]oct-2-ene-5-oxide (2.68 g) in the form of a hard cream-coloured foam.

Infra-red spectrum (CHBr$_3$), characteristic bands in cm$^{-1}$: 3,380, 1,800, 1,720, 1,670, 1,520, 1,495, 1,450, 1,045, 940 and 755.

Proton NMR spectrum (350 MHz, CDCl$_3$, δ in ppm, J in Hz): 3.32 and 4 (2d, J=18, 2H, -SCH$_2$-); 3.97 (s, 3H, -OCH$_3$); 4.60 (d, J=4, 1H, H in the 6-position); 5.0 (s, 2H, >NCH$_2$-); 6.02 (dd, J=4 and 9, 1H, H in the 7-position); 6.70 (s, 1H, H of the thiazole); 6.80 (d, J=16, 1H, -CH=CHS-); 6.94 (s, 1H, -COOCH-); and 11.87 (s broad, 1H, =N NHCO-).

A solution of the E form of the syn isomer of 2-benzhydryloxycarbonyl-3-[2-(4-benzyl-5,6-dioxo-1,4,5,6-tetrahydro-1,2,4-triazin-3-yl)-thiovinyl]-7-[2-methoxyimino-2-(2-tritylaminothiazol-4-yl)-acetamido]-8-oxo-5-thia-1-azabicyclo[4.2.0]oct-2-ene-5-oxide (2.68 g) in a mixture of methylene chloride (25 cc) and dimethylacetamide (0.95 cc) is treated for 30 minutes, at −10° C., whilst stirring, with phosphorus trichloride (0.44 cc). The mixture is diluted with ethyl acetate (200 cc) and the resulting mixture is washed with a 5% strength solution of sodium bicarbonate (50 cc), water (2×50 cc) and a saturated solution of sodium chloride (50 cc), dried over sodium sulphate and filtered and the filtrate is concentrated to dryness at 20° C. under 20 mm Hg (2.7 kPa). The product, fixed beforehand onto Merck silica gel (0.05–0.2) (20 g), is deposited on a column of silica gel (40 g) (diameter of the column: 1.4 cm, height: 15 cm). Elution is carried out with a mixture of cyclohexane/ethyl acetate (20/80 by volume) (1 liter), 60 cc fractions being collected. Fractions 2 to 13 are evaporated to dryness at 20° C. under 20 mm Hg (2.7 kPa). The E form of the syn isomer of 2-benzhydryloxycarbonyl-3-[2-(4-benzyl-5,6-dioxo-1,4,5,6-tetrahydro-1,2,4-triazin-3-yl)-thiovinyl]-7-[2-methoxyimino-2-(2-tritylaminothiazol-4-yl)-acetamido]-8-oxo-5-thia-1-azabicyclo[4.2.0]oct-2-ene (1.78 g) is collected in the form of a hard cream-coloured foam.

Infra-red spectrum (CHBr$_3$), characteristic bands in cm$^{-1}$: 3,390, 1,785, 1,720, 1,680, 1,520, 1,495, 1,450, 1,045 and 940.

Proton NMR spectrum (350 MHz, CDCl$_3$, δ in ppm, J in Hz): 3.54 and 3.64 (2d, J=18, 2H, -SCH$_2$-); 4.02 (s, 3H, -OCH$_3$); 5.06 (d, J=4, 1H, H in the 6-position); 5.10 (s, 2H, >NCH$_2$-); 5.92 (dd, J=4 and 9, 1H, H in the 7-position); 6.74 (s, 1H, H of the thiazole); 6.82 (d, J=16, 1H, -CH=CHS-); 6.95 (s, 1H, -COOCH-); 7.03 (d, J=9, 1H, -CONH-); and 11.60 (s, 1H, =NNH CO-).

A solution of the E form of the syn isomer of 2-benzhydryloxycarbonyl-3-[2-(4-benzyl-5,6-dioxo-1,4,5,6-tetrahydro-1,2,4-triazin-3-yl)-thiovinyl]-7-[2-methoxyimino-2-(2-tritylaminothiazol-4-yl)-acetamido]-8-oxo-5-thia-1-azabicyclo[4.2.0]oct-2-ene (1.78 g) in a mixture of formic acid (16 cc) and water (8 cc) is stirred at 50° C. for 30 minutes. The cooled solution is filtered and the filtrate is concentrated to dryness at 50° C. under 20 mm Hg (2.7 kPa). The residue is taken up in ethanol (50 cc), the mixture is evaporated to dryness at 20° C. under 20 mm Hg (2.7 kPa) and this operation is repeated twice. The resulting yellow solid is treated under reflux with ethanol (100 cc), a small amount of insoluble material is removed by filtration and the solution is concentrated to 50 cc (20° C., 20 mm Hg; 2.7 kPa). After cooling for 3 hours at 4° C., the precipitate is filtered off and dried and this yields the E form of the syn isomer of 7-[2-(2-aminothiazol-4-yl)-2-methoxyiminoacetamido]-3-[2-(4-benzyl-5,6-dioxo-1,4,5,6-tetrahydro-1,2,4-triazin-3-yl)-thiovinyl]-2-carboxy-8-oxo-5-thia-1-azabicyclo[4.2.0]oct-2-ene (0.69 g) in the form of a yellow powder.

Infra-red spectrum (KBr), characteristic bands in cm$^{-1}$: 3,500, 2,300, 1,770, 1,710, 1,680, 1,585, 1,530, 1,045 and 945.

Proton NMR spectrum (350 MHz, d$_6$-DMSO, δ in ppm, J in Hz): 3.58 and 3.78 (2d, J=18, 2H, -SCH$_2$-); 3.88 (s, 3H, -OCH$_3$); 5.10 (s, 2H, >NCH$_2$); 5.18 (d, J=4, 1H, H in the 6-position); 5.78 (dd, J=4 and 9, 1H, H in the 7-position); 6.75 (s, 1H, H of the thiazole); 6.86 (d, J=16, 1H, -CH=CHS-); 7.05 (d, J=16, 1H, =CHS-), 7.20 (s, 3H, -NH$_3$+); 9.60 (d, J=9, 1H, -CONH-); and 12.69 (s, 1H, =NNHCO-).

REFERENCE EXAMPLE 2

The product of Example 2 can be used as follows:

A mixture of the E form of the syn isomer of 2-benzhydryloxycarbonyl-7-[2-methoxyimino-2-(2-tritylaminothiazol-4-yl)-acetamido]-8-oxo-3-(2-tosyloxyvinyl)-5-thia-1-azabicyclo[4.2.0]oct-2-ene-5-oxide (8.03 g), dimethylformamide (150 cc), 5,6-dioxo-4-(2-methylthioethyl)-3-thioxo-perhydro-1,2,4-triazine (2.19 g) and diisopropylethylamine (1.7 cc) is stirred at 60° C. for 4 hours. The mixture is poured into ethyl acetate (300 cc), the resulting mixture is washed with water (3×200 cc) and a saturated solution of sodium chloride (200 cc), dried over sodium sulphate and filtered and the filtrate is concentrated to dryness at 20° C. under 20 mm Hg (2.7 kPa). The product, fixed beforehand onto Merck silica gel (0.05–0.2) (20 g), is chromatographed on silica gel (200 g) (diameter of the column: 3.4 cm, height: 40 cm). Elution is carried out successively with the following mixtures of cyclohexane/ethyl acetate: 40/60 (by volume) (500 cc), 30/70 (by volume (500 cc), 20/80 (by volume) (500 cc) and 10/90 (by volume) (500 cc), and is completed with pure ethyl acetate (2 liters), 120 cc fractions being collected. Fractions 22 to 32 are concentrated to dryness and this yields the E form of the syn isomer of 2-benzhydryloxycarbonyl-3-{2-[5,6-dioxo-4-(2-methylthioethyl)-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide (5.66 g) in the form of a hard cream-coloured foam.

Infra-red spectrum (KBr), characteristic bands in cm$^{-1}$: 1,795, 1,715, 1,670, 1,525, 1,495, 1,455, 1,040, 945, 755 and 700.

A solution of the E form of the syn isomer of 2-benzhydryloxycarbonyl-3-{2-[5,6-dioxo-4-(2-methylthioethyl)-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide (5.6 g) in a mixture of methylene chloride (53.8 cc) and dimethylacetamide (1.99 cc) is treated at −10° C., for 30 minutes, whilst stirring, with phosphorus trichloride (0.941 cc). The mixture is diluted with ethyl acetate (200 cc), the resulting mixture is washed successively with a saturated solution of sodium bicarbonate (100 cc), water (2×100 cc) and a saturated solution of sodium chloride (100 cc), dried over sodium sulphate and filtered and the filtrate is concentrated to dryness at 20° C. under 20 mm Hg (2.7 kPa).

The product is fixed onto Merck silica gel (0.05–0.2) (15 g) and the powder is deposited on a column of silica gel (100 g) (diameter of the column: 3 cm, height: 30 cm). Elution is carried out with a 20/80 (by volume) mixture of cyclohexane/ethyl acetate (1.5 liters), 60 cc fractions being collected. Fractions 3 to 18 are concentrated to dryness at 20° C. under 20 mm Hg (2.7 kPa). This yields the E form of the syn isomer of 2-benzhydryloxycarbonyl-3-{2-[5,6-dioxo-4-(2-methylthioethyl)-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (4.16 g) in the form of a hard yellow foam.

Infra-red spectrum (KBr), characteristic bands in cm$^{-1}$: 1,785, 1,715, 1,680, 1,525, 1,490, 1,445, 1,040, 940, 750 and 700.

Proton NMR spectrum (350 MHz, CDCl$_3$, δ in ppm, J in Hz): 2.18 (s, 3H, -SCH$_3$); 2.78 (t, J=6, 2H, -CH$_2$S-); 3.58 and 3.67 (d, J=18, 2H, -SCH$_2$-); 3.95 to 4.05 (m, 5H, -OCH$_3$ and >NCH$_2$-); 5.08 (d, J=4, 1H, H in the 6-position); 5.93 (dd, J=4 and 9, 1H, H in the 7-position); 6.74 (s, 1H, H of the thiazole); 6.82 (d, J=16, 1H, -CH=CHS-); 6.95 (s, 1H,

—COOCH—);
        | and 11.55 (s broad, 1H, =NNHCO-).

A solution of the E form of the syn isomer of 2-benzhydryloxycarbonyl-3-{2-[5,6-dioxo-4-(2-methylthioethyl)-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (4.16 g) in a mixture of formic acid (40 cc) and water (20 cc) is stirred at 50° C. for 30 minutes. The cooled mixture is then filtered and the filtrate is concentrated to dryness under reduced pressure (40° l C., 20 mm Hg; 2.7 kPa). The residue is taken up in ethanol (100 cc) and the mixture is concentrated to dryness at 20° C. under 20 mm Hg (2.7 kPa). This operation is repeated twice, the solid is then dissolved in boiling ethanol (250 cc) and the solution is filtered hot and concentrated to 20 cc (20° C., 20 mm Hg; 2.7 kPa). The precipitate is filtered off and dried and this yields the E form of the syn isomer of 7-[2-(2-aminothiazol-4-yl)-2-methoxyiminoacetamido]-2-carboxy-3-{2-[5,6-dioxo-4-(2-methylthioethyl)-1,4,5,6-tetrahydro-1,2,4-triazin-3-yl]-thiovinyl}-8-oxo-5-thia-1-azabicyclo[4.2.0]oct-2-ene (1.95 g).

Infra-red spectrum (KBr), characteristic bands in cm$^{-1}$: 3,600, 2,200, 1,770, 1,710, 1,680, 1,585, 1,535, 1,040 and 945.

Proton NMR spectrum (350 MHz, d$_6$-DMSO, δ in ppm, J in Hz): 2.12 (s, 3H, -SCH$_3$); 2.73 (t, J=7, 2H, -CH$_2$S-CH$_3$); 3.64 and 3.82 (2d, J=18, 2H, -SCH$_2$-); 3.85 (s, 3H, -OCH$_3$); 4.0 (t, J=7, 2H, >NCH$_2$-); 5.20 (d, J=4, 1H, H in the 6-position); 5.78 (dd, J=4 and 9, 1H, H in the 7-position); 6.73 (s, 1H, H of the thiazole); 6.92 (d, J=16, 1H, -CH=CHS-); 7.12 (d, J=16, 1H, =CHS-); 7.15 (s, 3H, -NH$_3^+$); 9.66 (d, J=9, 1H, -CONH-); and 12.61 (s, 1H =NNHCO-).

REFERENCE EXAMPLE 3

The product of Example 3 can be used as follows:

A mixture of the E form of the syn isomer of 2-benzhydryloxycarbonyl-7-[2-methoxyimino-2-(2-tritylaminothiazol-4-yl)-acetamido]-8-oxo-3-(2-tosyloxyvinyl)-5-thia-1-azabicyclo[4.2.0]oct-2-ene-5-oxide (10 g), dimethylformamide (50 cc), 4-(2,2-dimethoxyethyl)-5,6-dioxo-3-thioxo-perhydro-1,2,4-triazine (2.56 g) and N,N-diisopropylethylamine (1.9 cc) is stirred at 60° C. under nitrogen for 2 hours 30 minutes. The mixture is diluted with ethyl acetate (600 cc), the resulting mixture is washed with water (2×125 cc), 1 N hydrochloric acid (150 cc), a semi-saturated solution of sodium bicarbonate (2×150 cc) and a semi-saturated solution of sodium chloride (2×150 cc), dried over sodium sulphate and filtered and the filtrate is concentrated to dryness under reduced pressure (20° C., 20 mm Hg; 2.7 kPa). The residue, dissolved in methylene chloride (30 cc), is chromatographed on a column of Merck silica gel (0.02–0.06) (diameter of the column: 7 cm, height: 35 cm). Elution is carried out with a 40/60 (by volume) mixture of cyclohexane/ethyl acetate (7 liters) under a pressure of 40 kPa, 100 cc fractions being collected. Fractions 27 to 46 are concentrated to dryness at 20° C. under reduced pressure (20 mm Hg; 2.7 kPa). The E form of the syn isomer of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo-[4.2.0]oct-2-ene-5-oxide (8.5 g) is collected in the form of a hard beige-coloured foam.

Infra-red spectrum (KBr), characteristic bands in cm$^{-1}$: 3,380, 3,250, 1,795, 1,720, 1,685, 1,520, 1,490, 1,445, 1,040, 940, 760 and 700.

Proton NMR spectrum (350 MHz, CDCl$_3$, δ in ppm, J in Hz): 3.34 and 4.12 (2d, J=18, 2H, -SCH$_2$-); 3.40 (s, 6H, -OCH$_3$); 3.94 to 4.06 (m, 5H, -OCH$_3$ and >NCH$_2$-); 4.60 to 4.68 (m, 2H, H in the 6-position and -CH(OCH$_3$)$_2$); 6.07 (dd, J=4 and 9, 1H, H in the 7-position); 6.70 (s, 1H, H of the thiazole); 6.82 (d, J=16, 1H, -CH=CHS-); and 6.96 (s, 1H, -COOCH-).

A solution of the E form of the syn isomer of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-tritylaminothiazol-4-yl)-acetamido]-8-oxo-5-thia-1-azabicyclo[4.2.0]oct-2-ene-5-oxide (8.5 g) and dimethylacetamide (3 cc) in methylene chloride (100 cc) is treated at −10° C., whilst stirring, with phosphorus trichloride (1.40 cc); after 1 hour 30 minutes and then after 2 hours, phosphorus trichloride is added (0.7 cc each time). The mixture is diluted with ethyl acetate (600 cc), the resulting mixture is washed with a 2% strength solution of sodium bicarbonate (2×150 cc) and a semi-saturated solution of sodium chloride (2×150 cc), dried over sodium sulphate and filtered and the filtrate is concentrated to dryness at 20° C. under a pressure of 20 mm Hg (2.7 kPa). The residue is taken up in ethyl acetate (50 cc) and the solution is chromatographed on a column of Merck silica gel (0.05–0.2) (100 g) (diameter of the column: 3 cm, height: 25 cm). Elution is carried out with ethyl acetate (1 liter), 200 cc fractions being collected. Fractions 3, 4 and 5 are concentrated to dryness (20 mm Hg; 2.7 kPa) at 20° C. The E form of the syn isomer of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (7.5 g) is collected in the form of a hard orange foam.

Infra-red spectrum (CHBr$_3$), characteristic bands in cm$^{-1}$: 3,380, 1,780, 1,720, 1,680, 1,515, 1,490, 1,445, 755 and 740.

Proton NMR spectrum (350 MHz, CDCl$_3$, δ in ppm, J in Hz): 3.40 (s, 6H, -OCH$_3$); 3.54 and 3.66 (2d, J=18, 2H, -SCH$_2$-); 3.98 (d, J=5, 2H, >NCH$_2$-); 4.02 (s, 3H, =NOCH$_3$); 4.65 (t, J=5, 1H, -CH(OCH$_3$)$_2$); 5.08 (d, J=4, 1H, H in the 6-position); 5.92 (dd, J=4 and 9, 1H, H in the 7-position); 6.73 (s, 1H, H of the thiazole); 6.83 (d, J=16, 1H, -CH=CHS-); and 6.95 (s, 1H, -COOCH-).

(a) A solution of the E form of the syn isomer of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (1.05 g) in 98% strength formic acid (20 cc) is heated at 50° C. for 30 minutes. The mixture is concentrated to dryness at 50° C. under a pressure of 0.05 mm Hg (0.007 kPa), the residue is taken up in acetone (50 cc), the mixture is concentrated to dryness at 30° C. under reduced pressure (20 mm Hg; 2.7 kPa) and this operation is repeated a second time.

The resulting solid is treated with acetone (50 cc) at 60° C. for 10 minutes, whilst stirring, the cooled suspension is filtered, the residue is dried and this yields the E form of the syn isomer of 7-[2-(2-aminothiazol-4-yl)-2-methoxyiminoacetamido]-2-carboxy-3-{2-[5,6-dioxo-4-formylmethyl-1,4,5,6-tetrahydro-1,2,4-triazin-3-yl]-thiovinyl}-8-oxo-5-thia-1-azabicyclo[4.2.0]oct-2-ene (0.51 g).

Infra-red spectrum (KBr), characteristic bands in cm$^{-1}$: 3,500, 2,300, 1,770, 1,715, 1,680, 1,540, 1,050 and 950.

Proton NMR spectrum (350 MHz, CF$_3$COOD, δ in ppm, J in Hz): 3.87 (limiting AB-type, 2H, -SCH$_2$-); 4.30 (s, 3H, -OCH$_3$); 5.20 (s broad, 2H, >NCH$_2$-); 5.38 (d, J=4, 1H, H in the 6-position); 6.03 (d, J=4, 1H, H in the 7-position); 7.22 (d, J=16, 1H, -CH=CHS-); b 7.50 (s, 1H, H of the thiazole); 7.72 (d, J=16, 1H, =CHS-); and 9.74 (s broad, 1H, -CHO).

Proton NMR spectrum (350 MHz, CF$_3$COOD+D$_2$O, δ in ppm, J in Hz): 3.82 (limiting AB-type, 2H, -SCH$_2$-); 4.26 (s, 3H, -OCH$_3$); 5.10 (s broad, 2H, >NCH$_2$-); 5.31 (d, J=4, 1H, H in the 6-position); 5.96 (d, J=4, 1H H in the 7-position); 7.06 (d, J=16, 1H, -CH=CHS-); 7.43 (s, 1H, H of the thiazole); 7.56 (d, J=16, 1H, =CHS-); and 9.67 (s broad, 1H, -CHO).

(b) It is also possible to follow the procedure below:

A mixture of the E form of the syn isomer of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (1 g), pure formic acid (40 cc), water (1.27 cc) and Merck silica gel (0.05–0.2) (6 g) is heated at 50° C. for 30 minutes, whilst stirring. The mixture is concentrated to dryness at 30° C. under 20 mm Hg (2.7 kPa) and the resuling powder is deposited on a column of Merck silica gel (0.05–0.2) (20 g) (diameter of the column: 2 cm, height: 17 cm). Elution is carried out with a 3/1/1 (by volume) mixture of ethyl acetate/formic acid/water, 10 cc fractions being collected. Fractions 3 to 26 are concentrated to dryness at 27° C. under 0.05 mm Hg (0.007 kPa). The resulting yellow solid is triturated in ether (60 cc), the residue is filtered off and dried and this yields the E form of the syn isomer of 7-[2-(2-aminothiazol-4-yl)-2-methoxyiminoacetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (0.4 g), the NMR and infra-red characteristics of which are identical to those of the product of Reference Example 3 (a).

(c) A mixture of the E form of the syn isomer of 7-[2-(2-aminothiazol-4-yl)-2-methoxyiminoacetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (0.297 g), water (10 cc) and sodium bicarbonate (0.042 g) is stirred, under nitrogen, until the solids have dissolved, and the solution is filtered and lyophilised. The sodium salt of the aldehyde hydrate of the E form of the syn isomer of 7-[2-(2-aminothiazol-4-yl)-2-methoxyiminoacetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (0.28 g) is collected.

Infra-red spectrum (KBr), characteristic bands in cm$^{-1}$: 3,420, 3,200, 1,760, 1,710, 1,670, 1,600, 1,530, 1,040 and 945.

Proton NMR spectrum (350 MHz, d$_6$-DMSO+D$_2$O, δ in ppm, J in Hz): 3.54 (limiting AB-type, 2H, -SCH$_2$-); 5.06 (d, J=4, 1H, H in the 6-position); 5.08 (s, 1H, -CH(OH)$_2$); 5.63 (d, J=4, 1H, H in the 7-position); 6.44 (d, J=16, 1H, -CH=CHS-); 6.76 (s, 1H, H of the thiazole); 7.24 (d, J=16, 1H, =CHS-); and 9.60 (s, 0.05H, -CHO).

The NMR spectrum of this sodium salt of the aldehyde hydrate, run in CF$_3$COOD, shows that, in solution in this solvent, the product is in the form of the aldehyde [spectrum identical to that described in Reference Example 3 (a)].

REFERENCE EXAMPLE 4

The product of Example 4 can be used as follows:

The E form of the syn isomer of 2-benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide is prepared as described in Reference Example 3, but starting from tosylate (15.06 g) and 4-(2,2-diethoxyethyl)-5,6-dioxo-3-thioxo-perhydro-1,2,4-triazine (8 g), in the presence of N,N-diisopropylethylamine (2.85 cc), in dimethylformamide (75 cc). Chromatography is carried out on a column of Merck silica gel (0.05–0.2) (250 g) (diameter of the column: 5 cm, height: 40 cm), elution being carried out with a 30/70 (by volume) mixture of cyclohexane/ethyl acetate (5 liters). The expected product (8.35 g) is collected in the form of a hard red-brown foam.

Proton NMR spectrum (350 MHz, CDCl$_3$, δ in ppm, J in Hz): 1.15 (t, J=7, 6H, -CH$_3$); 3.38 (d, J=18, 1H, -SCH<); 3.50 and 3.72 (2q AB-type, J=9 and 7, 4H, -OCH$_2$-); 3.90 and 4.20 (hump, 6H, >NCH$_2$-, -OCH$_3$ and -SCH<); 4.65 (d, J=4, 1H, H in the 6-position); 4.72 (t, J=5, 1H, -C$\underline{\text{H}}$(OEt)$_2$); 6.04 (dd, J=4 and 9, 1H, H in the 7-position); 6.70 (s, 1H, H of the thiazole); 6.85 (d, J=16, 1H, -C$\underline{\text{H}}$=CHS-); 6.97 (s, 1H, -COOCH-); and 11.94 (s broad, 1H, =NNHCO-).

A solution of the E form of the syn isomer of 2-benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide (8.30 g) in methylene chloride (100 cc) and dimethylacetamide (2.88 cc) is treated at −10° C. for 2 hours with phosphorus trichloride (1.33 cc). The mixture is treated as described in Reference Example 3 (a), chromatography being carried out on a column of Merck silica gel (0.05–0.2) (200 g) (diameter of the column: 4 cm, height: 44 cm) and elution being carried out with a 30/70 (by volume) mixture of cyclohexane/ethyl acetate (2 liters). The E form of the syn isomer of 2-benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (5.3 g) is collected in the form of a hard orange-yellow foam. The product is purified by dissolving it in ethyl acetate (20 cc) and adding diisopropyl ether (100 cc); this yields a cream-coloured solid (4.5 g).

Infra-red spectrum (CHBr$_3$), characteristic bands in cm$^{-1}$: 3,390, 1,785, 1,720, 1,685, 1,585, 1,515, 1,495, 1,445, 1,050, 940, 750 and 740.

Proton NMR spectrum (350 MHz, CDCl$_3$, δ in ppm, J in Hz): 1.18 (t, J=7, 6H, -CH$_3$); 3.52 and 3.75 (2q AB-type, J=7 and 10, 4H, -OCH$_2$-); 3.60 (d, J=18, 1H, -SCH<); 3.97 to 4.06 (hump, 6H, -OCH$_3$, >NCH$_2$-, -SCH<); 4.76 (t, J=5, 1H, -C$\underline{\text{H}}$(OEt)$_2$); 5.09 (d, J=4, 1H, H in the 6-position); 5.92 (dd, J=4 and 9, 1H, H in the 7-position); 6.75 (s, 1H, H of the thiazole); 6.85 (d, J=16, 1H, -C$\underline{\text{H}}$=CHS-); 6.92 (d, J=9, 1H, -CONH-); 6.92 (s, 1H, -COOCH-); and 11.30 (s broad, 1H, =NNHCO-).

A solution of the E form of the syn isomer of 2-benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyamino-2-(2-tritylaminothiazol-4-yl)-acetamido]-8-oxo-5-thia-1-azabicyclo[4.2.0]oct-2-ene (1 g) in pure formic acid (25 cc) is heated at 50° C. for 30 minutes. The mixture is concentrated to dryness at 40° C. under 20 mm Hg (2.7 kPa), the residue is taken up in acetone (20 cc), the mixture is concentrated to dryness at 20° C. under 20 mm Hg (2.7 kPa), the operation is repeated twice, the residue is triturated in acetone (40 cc), the mixture is heated under reflux for 10 minutes, whilst stirring, and the cooled suspension is filtered. This yields a yellow powder (0.6 g) which is purified in the following manner:

The preceding product (50 mg) is dissolved in pure formic acid (5 cc), Merck silica gel (0.05–0.2) (2.5 g) is added and the mixture is concentrated to dryness at 30° C. under 0.05 mm Hg (0.007 kPa). The powder is deposited on a column of silica gel (5 g) (diameter of the column: 2.5 cm, height: 3 cm) and elution is carried out with a 3/2/2 (by volume) mixture of ethyl acetate/acetic acid/water, 10 cc fractions being collected. Fractions 2 to 7 are concentrated to dryness (30° C. under 0.05 mm Hg; 0.007 kPa) and this yields the E form of the syn isomer of 7-[2-(2-aminothiazol-4-yl)-2-methoxyiminoacetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]-oct-2-ene (30 mg) in the form of a cream-coloured powder, the infra-red and NMR characteristics of which are identical to those of the product of Reference Example 3 (a).

REFERENCE EXAMPLE 5

A mixture of the E form of the syn isomer of 2-benzhydryloxycarbonyl-7-[2-methoxyimino-2-(2-tritylaminothiazol-4-yl)-acetamido]-8-oxo-3-(2-tosyloxyvinyl)-5-thia-1-azabicyclo[4.2.0]oct-2-ene-5-oxide (5.02 g), dimethylformamide (93 cc), 4-(2,2-dimethyldioxolan-4-ylmethyl)-5,6-dioxo-3-thioxo-perhydro-1,2,4-triazine (1.5 g) and N,N-diisopropylethylamine (1.05 cc) is stirred at 60° C. for 3 hours, under nitrogen. The mixture is diluted with ethyl acetate (200 cc), the resulting mixture is washed with water (4×200 cc), dried over sodium sulphate and filtered and the filtrate is concentrated to dryness at 20° C. under 20 mm Hg (2.7 kPa). The residue is fixed onto Merck silica gel (0.06–0.2) (10 g) and the powder is deposited on a column of Merck silica gel (0.06–0.2) (100 g) (diameter of the column: 2.5 cm, height: 40 cm). Elution is carried out with ethyl acetate (1.3 liters), 60 cc fractions being collected. Fractions 6 to 20 are concentrated to dryness at 20° C. under 20 mm Hg (2.7 kPa) and the E form of the syn isomer of 2-benzhydryloxycarbonyl-3-{2-[4-(-2,2-dimethyldioxolan-4-yl-methyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2ene-5-oxide (2.48 g) is collected in the form of a hard yellow foam.

Proton NMR spectrum (350 MHz, CDCl$_3$, δ in ppm, J in Hz): 1.32 and 1.43 (2s, 6H, -C(CH$_3$)$_2$); 3.34 and 4.05 (2d, J=18, 2H,

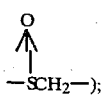

3.74 (t, J=6, 2H, -CH₂O-); 3.84 (s, 3H, =NOCH₃); 3.95 (t, J=6, 2H, >N-CH₂-); 4.38 (quintet, J=6, 1H, >CH-O-); 4.65 (d, J=4, 1H, H in the 6-position); 6.06 (dd, J=4 and 9, 1H, H in the 7-position); 6.71 (s, 1H, H of the thiazole); 6.84 (d, J=16, 1H, -CH=CHS-); 6.96 (s, 1H, -COOCH<); and 11.60 (s, 1H, =N-NHCO-).

A solution of the E form of the syn isomer of 2-benzhydryloxycarbonyl-3-{2-[4-(2,2-dimethyldioxolan-4-yl-methyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]-oct-2-ene-5-oxide (2.48 g) in methylene chloride (22.9 cc) and dimethylacetamide (0.85 cc) is treated at −10° C. for 40 minutes with phosphorus trichloride (0.4 cc). The mixture is poured into ethyl acetate (250 cc), the resulting mixture is washed successively with a saturated solution of sodium bicarbonate (200 cc), water (2×100 cc) and a saturated solution of sodium chloride (100 cc), dried over sodium sulphate and filtered and the filtrate is concentrated to dryness at 20° C. under 20 mm Hg (2.7 kPa). The residue is taken up in methylene chloride (20 cc), Merck silica gel (0.06–0.2) (10 g) is added, the mixture is concentrated to dryness at 20° C. under 20 mm Hg and the resulting powder is deposited on a column of Merck silica gel (0.06–0.2) (40 g) (diameter of the column: 1.5 cm, height: 15 cm). Elution is carried out with methylene chloride (500 cc), 60 cc fractions being collected. Fractions 2 to 7 are combined and concentrated to dryness at 20° C. under 20 mm Hg and the E form of the syn isomer of 2-benzhydryl oxycarbonyl-3-{2-[4-(2,2-dimethyldioxolan-4-yl-methyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (1.4 g) is collected in the form of a hard yellow foam.

A mixture of the E form of the syn isomer of 2-benzhydryloxycarbonyl-3-{2-[4-(2,2-dimethyldioxolan-4-yl-methyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]-oct-2-ene (1.4 g), formic acid (13 cc) and water (6.5 cc) is heated at 50° C. for 30 minutes. The mixture is cooled to 20° C. and filtered and the filtrate is concentrated to dryness at 30° C. under 0.05 mm Hg (0.007 kPa). The residue is taken up in ethanol (100 cc), the solvent is driven off at 20° C. under 20 mm Hg (2.7 kPa) and the operation is repeated twice. The yellow solid is taken up in boiling ethanol (100 cc), the mixture is filtered, the filtrate is concentrated to 50 cc at 20° C. (20 mm Hg; 2.7 kPa) and filtered and the solid is washed with diethyl ether (20 cc) and dried. The E form of the syn isomer of 7-[2-(2-aminothiazol-4-yl)-2-methoxyiminoacetamido]-2-carboxy-3-{2-[4-(2,3-dihydroxypropyl)-5,6-dioxo-1,4,5,6-tetrahydro-1,2,4-triazin-3-yl]-thiovinyl}-8-oxo-5-thia-1-azabicyclo[4.2.0]oct-2-ene (0.49 g) is collected.

NMR shows that this product contains about 25% of the formic acid ester of one or other of the alcohol groups.

Infra-red spectrum (KBr), characteristic bands (cm⁻¹): 3,650–2,200, 1,770, 1,710, 1,680, 1,590, 1,530, 1,045 and 945.

Proton NMR spectrum (350 MHz, d₆-DMSO+D₂O, δ in ppm, J in Hz): diol: 3.87 (s, 3H, =NOCH₃); 5.20 (d, J=4, 1H, H in the 6-position); 5.75 (d, J=4, H in the 7-position); 6.74 (s, 1H, H of the thiazole); 6.95 and 7.10 (2d, J=16, 2H, -CH=CH-S-); formic acid ester: 3.87 (s, 3H, =NOCH₃); 5.18 (d, J=4, 1H, H in the 6-position); 5.75 (d, J=4, 1H, H in the 7-position); 6.74 (s, 1H, H of the thiazole); 6.93 and 7.08 (2d, J=16, 2H, -CH=CHS-); and 8.22 (s, 1H, HCOO-).

2-Benzhydryloxycarbonyl-7-[2-methoxyimino-2-(2-tritylaminothiazol-4-yl)-acetamido]-8-oxo-3-(2-tosyloxyvinyl)-5-thia-1-azabicyclo[4.2.0]oct-2-ene-5-oxide (syn isomer, E form and Z form) can be prepared in the following manner:

Dicyclohexylcarbodiimide (1.85 g) is added, whilst stirring, to a solution, cooled to +4° C. of syn-2-methoxyimino-2-(2-tritylaminothiazol-4-yl)-acetic acid (7.97 g) in methylene chloride (100 cc). The solution is stirred for 40 minutes at +4° C. and then for 30 minutes at 20° C. and filtered.

A solution of crude 7-amino-2-benzhydryloxycarbonyl-8-oxo-3-(2-tosyloxyvinyl)-5-thia-1-azabicyclo-[4.2.0]oct-2-ene-5-oxide (mixture of the E and Z forms) (3.47 g) in methylene chloride (30 cc), to which triethylamine (0.84 cc) has been added, is added rapidly to the said filtered solution, cooled to −30° C. The cooling bath is removed as soon as the addition has ended, and the reaction mixture is stirred for 1 hour 50 minutes at 20° C. It is concentrated to dryness at 20° C. under reduced pressure (20 mm Hg) and the residue is taken up in ethyl acetate (250 cc). The organic phase is washed with water (3×100 cc), 0.05 N hydrochloric acid (100 cc), a 1% strength sodium bicarbonate solution (100 cc) and water semi-saturated with sodium chloride (2×100 cc), dried over sodium sulphate and filtered and the filtrate is concentrated to dryness under reduced pressure (20 mm Hg at 20° C.). The residue is taken up in ethyl acetate (20 cc), cyclohexane (20 cc) is added and the solution is filtered and chromatographed on a column of Merck silica gel (0.04–0.06 mm) (300 g) (diameter of the column: 6 cm, height: 30 cm). Elution is carried out with a 40/60 (by volume) mixture of cyclohexane/ethyl acetate (4 liters) under a pressure of 40 kPa, 125 cc fractions being collected. Fractions 6 to 25 are concentrated under reduced pressure (20 mm Hg) at 20° C.; 2-benzhydryloxycarbonyl-7-[2-methoxyimino-2-(2-tritylaminothiazol-4-yl)-acetamido]-8-oxo-3-(2-tosyloxyvinyl)-5-thia-1-azabicyclo[4.2.0]oct-2-ene-5-oxide (syn isomer, mixture of the E and Z forms) (4.8 g) is collected in the form of a hard cream-coloured foam.

By carrying out a second chromatographic separation which is identical to the previous separation, the Z isomer (1.21 g) is separated out in fractions 12 to 16 and the E isomer (1.49 g) is separated out in fractions 22 to 40; fractions 17 to 21 contain a mixture of E and Z (0.8 g).

Z isomer:

Infra-red spectrum (CHBr₃), characteristic bands (cm⁻¹): 3,380, 1,800, 1,720, 1,680, 1,510, 1,375, 1,190, 1,175, 1,045, 1,000 and 735.

Proton NMR spectrum (350 MHz, CDCl₃, δ in ppm, J in Hz): 2.03 (s, 3H, -C₆H₄-CH₃); 3.36 and 4.07 (2d, J=19, 2H, -SCH₂-); 4.09 (s, 3H, -OCH₃); 4.52 (d, J=4, 1H, H in the 6-position); 6.16 (dd, J=4 and 9, 1H, H in the 7-position); 6.43 (AB-type, J=8, 2H, -CH=CH-); 6.86 (s, 1H,

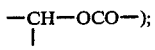

6.71 (s, 1H, H in the 5-position of the thiazole); and 7.75 (d, J=9, 2H, H in the ortho-position of the tosyl).

E isomer:

Infra-red spectrum (CHBr$_3$), characteristic bands (cm$^{-1}$): 3,380, 1,800, 1,725, 1,685, 1,515, 1,380, 1,190, 1,180, 1,070, 1,050, 755 and 735.

Proton NMR spectrum (350 MHz, CDCl$_3$, δ in ppm, J in Hz): 2.45 (s, 3H, -C$_6$H$_4$CH$_3$); 3.19 and 3.77 (2d, J=18, 2H, -SCH$_2$-); 4.08 (s, 3H, -OCH$_3$); 4.6 (d, J=4, H in the 6-position); 6.18 (dd, J=4 and 9, H in the 7-position); 6.72 (s, 1H, H in the 5-position of the thiazole); 6.93 (d, J=12, 1H, -CH=CH-OSO$_2$-); 7.11 (d, J=12, 1H, -CH=CHOSO$_2$-); 6.90 (s, 1H,

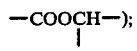

and 7.73 (d, J=9, 2H, H in the ortho-position of the tosyl).

7-Amino-2-benzhydryloxycarbonyl-8-oxo-3-(2-tosyloxyvinyl)-5-thia-1-azabicyclo[4.2.0]oct-2-ene-5-oxide (mixture of the E and Z forms) can be prepared in the following manner:

A solution of 2-benzhydryloxycarbonyl-7-t-butoxycarbonylamino-8-oxo-3-(2-tosyloxyvinyl)-5-thia-1-azabicyclo[4.2.0]oct-2-ene-5-oxide (mixture of the E and Z forms) (4.06 g) in acetonitrile (150 cc) is stirred at 20° C. for 16 hours with p-toluenesulphonic acid monohydrate (2.28 g). The mixture is concentrated under reduced pressure (20 mm Hg) at 20° C. to a volume of 10 cc and diluted with ethyl acetate (150 cc) and the mixture is washed with a 2% strength solution of sodium bicarbonate (100 cc) and then with water saturated with sodium chloride (2×150 cc), dried over sodium sulphate and concentrated to dryness under reduced pressure (20 mm Hg) at 20° C. 7-Amino-2-benzhydryloxycarbonyl-8-oxo-3-(2-tosyloxyvinyl)-5-thia-1-azabicyclo[4.2.0]oct-2-ene-5-oxide (mixture of the E and Z forms) (3.5 g) is collected in the form of a crude brown solid.

Infra-red spectrum (KBr), characteristic bands (cm$^{-1}$): 3,430, 3,360, 1,780, 1,725, 1,370, 1,180, 1,170, 1,070, 745 and 700.

Proton NMR spectrum (350 MHz, CDCl$_3$, δ in ppm, J in Hz): 2.43 (s, 3H, -CH$_3$); 3.12 and 3.75 (2d, J=18, 2H, -SCH$_2$-); 4.36 (d, J=4, 1H, H in the 6-position); 4.74 (d, J=4, 1H, H in the 7-position); 6.87 (d, J=12, 1H, -CH=CHOSO$_2$-); 6.90 (s, 1H,

6.99 (d, J=12, 1H, =CHOSO$_2$-); and 7.40 and 7.71 (2d, J=9, -C$_6$H$_4$-).

2-Benzhydryloxycarbonyl-7-t-butoxycarbonylamino-8-oxo-3-(2-tosyloxyvinyl)-5-thia-1-azabicyclo[4.2.0]oct-2-ene-5-oxide can be prepared in the following manner:

A solution of 85% strength m-chloroperbenzoic acid (55.22 g) in methylene chloride (600 cc) is added dropwise, in the course of 2 hours, to a solution, cooled to −10° C., of 2-benzhydryloxycarbonyl-7-t-butoxycarbonylamino-8-oxo-3-(2-tosyloxyvinyl)-5-thia-1-azabicyclo[4.2.0]oct-2-ene (or -3-ene) (mixture of the E and Z forms) (180.56 g) in methylene chloride (1.4 liters). The mixture is washed with a 5% strength solution of sodium bicarbonate (1.5 liters) and with water (2×1.5 liters), dried over sodium sulphate and concentrated at 20° C. under reduced pressure (20 mm Hg) to a volume of 300 cc. This solution is chromatographed on a column of Merck silica gel (0.05-0.2 mm) (3 kg) (diameter of the column: 9.2 cm, height: 145 cm). Elution is carried out successively with the following mixtures of cyclohexane/ethyl acetate: 80/20 (by volume) (15 liters) and 70/30 (by volume) (32 liters), 600 cc fractions being collected. Fractions 27 and 28 are collected and concentrated to dryness and this yields the Z form of 2-benzhydryloxycarbonyl-7-t-butoxycarbonylamino-8-oxo-3-(2-tosyloxyvinyl)-5-thia-1-azabicyclo[4.2.0]oct-2-ene-5-oxide (5.56 g).

Infra-red spectrum (CHBr$_3$), characteristic bands (cm$^{-1}$): 3,420, 1,800, 1,720, 1,505, 1,380, 1,370, 1,195, 1,180, 1,050, 1,010 and 730.

Proton NMR spectrum (350 MHz, CDCl$_3$, δ in ppm, J in Hz): 1.49 (s, 9H, -C(CH$_3$)$_3$); 2.44 (s, 3H, -CH$_3$); 3.36 and 4.04 (2d, J=19, 2H, -SCH$_2$-); 4.44 (d, J=4.5, 1H, H in the 6-position); 5.73 (d, J=9, 1H, -CONH-); 5.81 (dd, J=4.5 and 9, 1H, H in the 7-position); 6.42 (d, J=7, 1H, -CH=CHOSO$_2$-); 6.46 (d, J=7, 1H, =CHOSO$_2$-); 6.89 (s, 1H,

and 7.77 (d, J=9, 2H, H in the ortho-position of the tosyl).

A mixture of the Z and E forms (26 g) is obtained in fractions 29 to 34.

Finally, the E form of the product (43 g) is obtained in fractions 35 to 58:

Infra-red spectrum (CHBr$_3$), characteristic bands (cm$^{-1}$): 3,420, 1,800, 1,720, 1,505, 1,380, 1,370, 1,195, 1,180, 1,075, 935 and 745.

Proton NMR spectrum (350 MHz, CDCl$_3$, δ in ppm, J in Hz): 1.48 (s, 9H, (CH$_3$)$_3$C-); 2.46 (s, 3H, -CH$_3$); 3.16 and 3.81 (2d, J=18, 2H, -SCH$_2$-); 4.46 (d, J=4.5, 1H, H in the 6-position); 5.73 (d, J=9, 1H, -CONH-); 5.8 (dd, J=9 and 4.5, 1H, H in the 7-position); 6.83 (d, J=13, 1H, -CH=CHOSO$_2$-); 6.83 (s, 1H,

7.08 (d, J=13, 1H, =CHOSO$_2$-); and 7.73 (d, J=9, 2H, H in the ortho-position of the tosyl).

2-Benzhydryloxycarbonyl-7-t-butoxycarbonylamino-8-oxo-3-(2-tosyloxyvinyl)-5-thia-1-azabicyclo[4.2.0]oct-2-ene (mixture of the E and Z forms) can be obtained in the following manner:

A solution of formic acid (50 cc) in water (500 cc) is added to a solution of 2-benzhydryloxycarbonyl-7-t-butoxycarbonylamino-3-(2-dimethylaminovinyl)-8-oxo-5-thia-1-azabicyclo[4.2.0]oct-2-ene (E form) (113.7 g) in tetrahydrofuran (1 liter). The homogeneous solution is stirred at 20° C. for 20 minutes and is then concentrated to a quarter of its volume under reduced pressure (20 mm Hg) at 20° C. The concentrate is taken up in ethyl acetate (2 liters), the mixture is washed with a 5% strength solution of sodium bicarbonate (2×500 cc), water (2×500 cc) and a saturated solution of sodium chloride (2×500 cc), dried over sodium sulphate and filtered and the filtrate is evaporated to dryness at 20° C. under reduced pressure (20 mm Hg). A crude product (112.4 g) is collected, which is treated in solution in anhydrous pyridine (250 cc), at 5° C., with tosyl chloride (57.2 g). After 30 minutes at 5° C. and 1 hour at 20° C., the solution is poured into a mixture of water/crushed ice (1 liter). The aqueous phase is separated off and the insoluble material is washed with distilled water (300 cc). The pasty product is dissolved in ethyl acetate (200 cc) and the solution is washed with 1 N hydrochloric acid (2×750 cc), a 5% strength solution of sodium bicarbonate (2×750 cc) and water (4×750 cc), dried over sodium sulphate and concentrated to dryness under reduced pressure (20 mm Hg) at 20° C. This yields a product (121 g) which consists mainly of 2-benzhydryloxycarbonyl-7-t-butoxycarbonylamino-8-oxo-3-(2-tosyloxyvinyl)-5-thia-1-azabicyclo[4.2.0]oct-2-ene (mixture of the E and Z forms) in the form of a brown foam.

2-Benzhydryloxycarbonyl-7-t-butoxycarbonylamino-3-(2-dimethylaminovinyl)-8-oxo-5-thia-1-azabicyclo-[4.2.0]oct-2-ene (E form) can be obtained by following the procedure below:

2-Benzhydryloxycarbonyl-7-t-butoxycarbonylamino-3-methyl-8-oxo-5-thia-1-azabicyclo[4.2.0]oct-2-ene (90.5 g) is dissolved in anhydrous N,N-dimethylformamide (400 cc). The resulting solution is heated to 80° C. under a nitrogen atmosphere. A solution of bisdimethylamino-t-butoxymethane (36.1 g) in anhydrous N,N-dimethylformamide (60 cc), preheated to 80° C., is then added rapidly. The reaction mixture is kept at 80° C. for 5 minutes and then poured into ethyl acetate (3 liters). After adding distilled water (1 liter), the organic phase is decanted, washed with distilled water (4×1 liter), dried over sodium sulphate and filtered in the presence of decolourising charcoal. The filtrate is concentrated to dryness under reduced pressure (20 mm Hg) at 30° C. and this yields 2-benzhydryloxycarbonyl-7-t-butoxycarbonylamino-3-(2-dimethylaminovinyl)-8-oxo-5-thia-1-azabicyclo[4.2.0]oct-2-ene (E form) (101 g) in the form of a hard orange foam.

RF=0.29; silica gel chromatography plate [cyclohexane/ethyl acetate, 50/50 (by volume)].

2-Benzhydryloxycarbonyl-7-t-butoxycarbonylamino-3-methyl-8-oxo-5-thia-1-azabicyclo[4.2.0]oct-2-ene can be obtained in the following manner:

A solution of diphenyldiazomethane (116.5 g) in acetonitrile (800 cc) is added dropwise, in the course of 45 minutes, at a temperature between 25° and 30° C., to a solution of 7-t-butoxycarbonylamino-2-carboxy-3-methyl-8-oxo-5-thia-1-azabicyclo[4.2.0]oct-2-ene (188.6 g) in acetonitrile (2,100 cc). The reaction mixture is stirred for 16 hours at 22° C. and then concentrated to dryness under reduced pressure (20 mm Hg) at 40° C. The residue is redissolved in ethyl acetate (2 liters) and the solution is washed with 2 N hydrochloric acid (700 cc) and then with a saturated aqueous solution of sodium bicarbonate (700 cc) and a saturated aqueous solution of sodium chloride (700 cc). The solution is dried over sodium sulphate, treated with decolourising charcoal and filtered and the filtrate is then concentrated to dryness under reduced pressure (20 mm Hg) at 40° C. The residue is dissolved in ethyl acetate (600 cc) at the boil. Cyclohexane (1 liter) is added and the mixture is heated to the reflux temperature and then left to cool. The crystals which have appeared are filtered off, washed with diethyl ether (3×250 cc) and then dried. This yields 2-benzhydryloxycarbonyl-7-t-butoxycarbonylamino-3-methyl-8-oxo-5-thia-1-azabicyclo[4.2.-0]oct-2-ene (191 g) in the form of white crystals (m.p.=179° C.) By concentrating the mother liquors to 500 cc, a second fraction of product (32.6 g, m.p.=178° C.) is obtained.

7-t-Butoxycarbonylamino-2-carboxy-3-methyl-8-oxo-5-thia-1-azabicyclo[4.2.0]oct-2-ene can be obtained in the following manner:

7-Amino-2-carboxy-3-methyl-8-oxo-5-thia-1-azabicyclo[4.2.0]oct-2-ene (371 g) is dissolved in a solution of sodium bicarbonate (307 g) in a mixture of distilled water (2 liters) and dioxane (2 liters). A solution of di-t-butyl dicarbonate (421 g) in dioxane (2 liters) is added in the course of 10 minutes. The reaction mixture is stirred for 48 hours at 25° C. The resulting suspension is concentrated under reduced pressure (20 mm Hg) at 50° C. to a residual volume of about 2 liters and is then diluted with ethyl acetate (1 liter) and distilled water (2 liters). The aqueous phase is separated off by decantation, washed with ethyl acetate (500 cc) and acidified to pH=2 with 6 N hydrochloric acid, in the presence of ethyl acetate (1,500 cc). The aqueous phase is extracted with ethyl acetate (2×1 liter). The combined organic phases are washed with a saturated solution of sodium chloride (2×250 cc) and dried over sodium sulphate. After filtration, the solvent is evaporated off under reduced pressure (20 mm Hg; 2.7 kPa) at 50° C. This yields 7-t-butoxycarbonylamino-2-carboxy-3-methyl-8-oxo-5-thia-1-azabicyclo[4.2.0]oct-2-ene (486 g) in the form of yellow crystals (m.p.=190° C., decomposition).

REFERENCE EXAMPLE 6

A mixture of the E form of the syn isomer of 2-benzhydryloxycarbonyl-7-[2-methoxyimino-2-(2-tritylaminothiazol-4-yl)-acetamido]-8-oxo-3-(2-tosyloxyvinyl)-5-thia-1-azabicyclo[4.2.0]oct-2-ene-5-oxide (10.04 g), dimethylformamide (200 cc), 4-(2-t-butoxycarbonylaminoethyl)-5,6-dioxo-3-thioxo-perhydro-1,2,4-triazine (3.46 g) and N,N-diisopropylethylamine (2.1 cc) is stirred at 60° C. for 3 hours 30 minutes. The mixture is diluted with ethyl acetate (800 cc), the resulting mixture is washed with a semi-saturated solution of sodium chloride (400 cc), dried over sodium sulphate and filtered and the filtrate is concentrated to dryness at 30° C. under 20 mm Hg (2.7 kPa). The product is chromatographed in solution in methylene chloride (50 cc) on a column of Merck silica gel (0.06–0.2) (100 g) (diameter of the column: 3 cm, height: 30 cm). Elution is carried out with a 50/50 (by volume) mixture of cyclohexane/ethyl acetate (500 cc), a 25/75 (by volume) mixture of cyclohexane/ethyl acetate (500 cc) and ethyl acetate (1.5 liters), 125 cc fractions being collected. Fractions 9 to 21 are concentrated to dryness (under 20 mm Hg; 2.7 kPa, at 20° C.) and the E form of the syn isomer of 2-benzhydryloxycarbonyl-3-{2-[4-(2-t-butoxycarbonylaminoethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide (7.69 g) is collected in the form of a hard brown foam.

Infra-red spectrum (KBr), characteristic bands (cm$^{-1}$): 3,380, 1,795, 1,715, 1,690, 1,590, 1,520, 1,495, 1,445, 1,205, 1,160, 1,040, 940, 750 and 700.

Proton NMR spectrum (350 MHz, CDCl$_3$, δ in ppm, J in Hz): 1.36 (s, 9H, -C(CH$_3$)$_3$); 3.30 and 4.65 (2d, J=18, 2H, -SCH$_2$-); 3.38 (m, 2H, -CH$_2$NHCO-); 3.95 (m, 2H, -CH$_2$-CH$_2$NH-); 4.0 (s, 3H, CH$_3$ON=); 5.20 (d, J=4, H$_6$); 6.03 (dd, J=4 and 9, H$_7$); 6.70 (s, H of the thiazole); 6.86 (d, J=16, -CH=CHS-); 6.94 (s, -COO-CH<); and 11.7 (s broad, -NH- of the triazine).

A solution of the E form of the syn isomer of 2-benzhydryloxycarbonyl-3-{2-[4-(2-t-butoxycarbonylaminoethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-:azabicyclo[4.2.0]oct-2-ene-5-oxide (3.36 g) in methylene chloride (30 cc) and dimethylacetamide (1.2 cc) is treated at −10° C. for 1 hour 30 minutes, whilst stirring, with phosphorus trichloride (1.04 cc). The mixture is diluted with ethyl acetate (250 cc), the resulting mixture is washed with a 2% strength solution of sodium bicarbonate (150 cc) and water semi-saturated with sodium chloride (2×100 cc), dried over sodium sulphate and filtered and the filtrate is concentrated to dryness at 20° C. under 20 mm Hg (2.7 kPa). The product is fixed onto Merck silica gel (0.06–0.2) (5 g) and chromatographed on a column of Merck silica gel (0.06–0.2) (50 g) (diameter of the column: 3 cm, height: 15 cm). Elution is carried out with ethyl acetate (6 liters), 600 cc fractions being collected. Fractions 2 to 7 are concentrated to dryness at 20° C. under 20 mm Hg (2.7 kPa) and the E form of the syn isomer of 2-benzhydryloxycarbonyl-3-{2-[4-(2-t-butoxycarbonylaminoethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]-oct-2-ene (1.97 g) is collected in the form of a hard yellow foam.

Infra-red spectrum (KBr), characteristic bands (cm$^{-1}$): 3,400, 3,280, 1,790, 1,715, 1,695, 1,590, 1,520, 1,495, 1,450, 1,040, 945, 755 and 700.

Proton NMR spectrum (350 MHz, DMSO, δ in ppm, J in Hz): 1.33 (s, 9H, -C(CH$_3$)$_3$); 3.20 (m, 2H, -CH$_2$CH$_2$N<); 3.64 and 3.86 (2d, J=18, 2H, -SCH$_2$-); 3.83 (t, J=6, 2H, -CH$_2$-CH$_2$N<); 3.84 (s, 3H, =NOCH$_3$); 5.25 (d, J=4, 1H, H$_6$); 5.77 (dd, J=4 and 9, 1H, H$_7$); 6.72 (s, 1H, H of the thiazole); 6.92 (s, 1H, -COOCH<); 9.93 and 7.02 (2d, J=12, 2H, -CH=CH-S); 8.82 (s, 1H, -NH-); 9.58 (d, J=9, 1H, -NHCO-); and 12.55 (s, 1H, -NH- of the triazine).

A mixture of the E form of the syn isomer of 2-benzhydryloxycarbonyl-3{2-[4-(2-t-butoxycarbonylaminoethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (1.88 g), formic acid (35 cc) and water (15 cc) is heated at 50° C. for 30 minutes. Water (20 cc) is then added, the mixture is left to cool to 20° C. and filtered and the filtrate is concentrated to dryness at 50° C. under 0.05 mm Hg (0.007 kPa). The residue is taken up in ethanol (2×100 cc), concentrating to dryness each time at 20° C. under 20 mm Hg (2.7 kPa). The residue is treated with ethanol (50 cc) at 45° C. for 15 minutes, the mixture is filtered and the solid is washed with ether (2×20 cc) and dried. The E form of the syn isomer of 7-[2-(2-aminothiazol-4-yl)-2-methoxyiminoacetamido]-3-{2-[4-(2-aminoethyl)-5,6-dioxo-1,4,5,6-tetrahydro-1,2,4-triazin-3-yl]-thiovinyl}-2-carboxy-8-oxo-5-thia-1-azabicyclo[4.2.0]oct-2-ene (1.08 g) is collected, as the formate, in the form of a yellow powder.

Infra-red spectrum (KBr), characteristic bands (cm$^{-1}$): 3,500, 2,200, 1,770, 1,710, 1,680, 1,630, 1,530, 1,380, 1,040 and 930.

Proton NMR spectrum (350 MHz, DMSO, δ in ppm, J in Hz): 3.12 (m, 2H, -CH$_2$-Ch$_2$-NH$_2$); 3.51 and 3.60 (2d, J=18, 2H, -SCH$_2$-); 3.85 (s, 3H, CH$_3$ON=); 4.12 (t, J=6, 2H, >NCH$_2$-CH$_2$-NH$_2$); 5.12 (d, J=4, 1H, H$_6$); 5.67 (dd, J=4 and 9, 1H, H$_7$); 6.44 (d, J=8, 1H, -CH=CHS-); 6.73 (s, 1H, H of the thiazole); 7.2 (s broad, 2H, -NH$_2$); 8.18 (s, 1H, H of the formate); and 9.55 (d, J=9, 1H, -NHCO-).

REFERENCE EXAMPLE 7

N,N'-Dicyclohexylcarbodiimide (1.11 g) is added to a suspension, cooled to 4° C., of the syn isomer of 2-methoxyimino-2-(2-tritylaminothiazol-4-yl)-acetic acid (2.17 g) and 4-(2-t-butoxycarbonylaminoethyl))-5,6-dioxo-3-thioxo-perhydro-1,2,4-triazine (1.05 g) in ethyl acetate (50 cc). The mixture is stirred for 4 hours at 20° C. and filtered and the filtrate is concentrated to dryness at 20° C. under 20 mm Hg (2.7 kPa). The residue is taken up in methylene chloride (20 cc) and the solution is poured into diisopropyl ether (250 cc). After filtration and drying, the syn isomer of 4-(2-t-butoxycarbonylaminoethyl)-5,6-dioxo-3-[2-methoxyimino-2-(2-tritylaminothiazol-4-yl)-acetylthio]-1,4,5,6-tetrahydro-1,2,4-triazine (0.73 g) is collected in the form of a yellow powder.

Infra-red spectrum (CHBr$_3$), characteristic bands (cm$^{-1}$): 3,440, 3,390, 2,820, 1,710, 1,585, 1,530, 1,450, 1,390, 1,370, 1,050, 955, 900 and 755.

A mixture of the E form of 7-amino-2-benzhydryloxycarbonyl-8-oxo-3-(2-tosyloxyvinyl)-5-thia-1-azabicyclo-[4.2.0]oct-2-ene-5-oxide (0.614 g), dimethylformamide (50 cc) and the syn isomer of 4-(2-t-butoxycarbonylaminoethyl)-5,6-dioxo-3-[2-methoxyimino-2-(2-tritylaminothiazol-4-yl)-acetylthio]-1,4,5,6-tetrahydro-1,2,4-triazine (0.70 g) is heated at 60° C. for 6 hours, under nitrogen. The mixture is diluted with ethyl acetate (150 cc), the resulting mixture is washed with water (2×120 cc), 1 N hydrochloric acid (2×100 cc), water (100 cc) and water saturated with sodium chloride (100 cc), dried over sodium sulphate and filtered and the filtrate is concentrated to dryness at 20° C. under 20 mm Hg (2.7 kPa). The residue is chromatographed on a column of Merck silica gel (0.06–0.2) (40 g) (diameter of the column: 2.5 cm, height: 29 cm). Elution is carried out with ethyl acetate (1 liter), 60 cc fractions being collected. Fractions 3 to 6 are concentrated to dryness at 20° C. under 20 mm Hg (2.7 kPa). The E form of the syn isomer of 2-benzhydryloxycarbonyl-3-{2-[4-(2-t-butoxycarbonylaminoethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide (0.21 g) is collected in the form of a hard brown foam.

By treating this product as described above in Reference Example 6, the E form of the syn isomer of 7-[2-(2-aminothiazol-4-yl)-2-methoxyiminoacetamido]-3-{2-[4-(2-aminoethyl)-5,6-dioxo-1,4,5,6-tetrahydro-1,2,4-triazin-3-yl]-thiovinyl}-2-carboxy-8-oxo-5-thia-1-azabicyclo[4.2.0]oct-2-ene is obtained as the formate, the characteristics of which are identical to those of the product of Reference Example 6.

REFERENCE EXAMPLE 8

A mixture of the E form of the syn isomer of 2-benzhydryloxycarbonyl-7-[2-methoxyimino-2-(2- tritylaminothiazol-4-yl)-acetamido]-8-oxo-3-(2-tosyloxyvinyl)-5-thia-1-azabicyclo[4.2.0]oct-2-ene (4.94 g), dimethylformamide (60 cc) and the sodium salt of 4-(3,3-diethoxy-2-hydroxypropyl)-5,6-dioxo-3-thioxo-perhydro-1,2,4-triazine (1.56 g) is stirred at 50° C. for 3 hours 30 minutes, under nitrogen. After treatment as in Reference Example 6 and chromatography on Merck silica gel (0.06-0.2) (150 g) (diameter of the column: 3 cm, height: 77 cm), elution being carried out with ethyl acetate, the E form of the syn isomer of 2-benzhydryloxycarbonyl-3-{2-[4-(3,3-diethoxy-2-hydroxypropyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (4.8 g) is collected in the form of a hard cream foam.

Infra-red spectrum (CHBr₃), characteristic bands (cm⁻¹): 3,540, 3,390, 3,200, 1,785, 1,715, 1,680, 1,585, 1,515, 1,495, 1,445, 1,045, 940, 755 and 740.

Proton NMR spectrum (350 MHz, CDCl₃, δ in ppm, J in Hz): 1.22 and 1.26 (2t, J=7, 6H, -CH₃); 2.78 (s broad, 1H, -OH); 3.60 and 4.01 (2d, J=18, 2H, -S-CH₂-); 3.50 to 3.80 (mt, 5H, (-OCH₂-)₂+-CHOH-); 4.02 (s, 3H, =N-OCH₃); 4.10 (mt, 2H, >N-CH₂-); 4.48 (d, J=6, 1H,

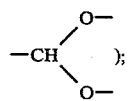

5.08 (d, J=4, 1H, -H in the 6-position); 5.92 (dd, J=4 and 9, 1H, -H in the 7-position); 6.72 (s, 1H, -H of the thiazole); 6.83 and 6.84 (2d, J=16, 1H, -CH=CH-S-); 6.94 (s, 1H, -COO-CH(C₆H₅)₂); 7.1 and 7.13 (2d, J=9, 1H, -CO-NH-); and 11.38 (hump, 1H, =N-NH-CO- or

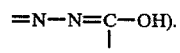

A solution of the E form of the syn isomer of 2-benzhydryloxycarbonyl-3-{2-[4-(3,3-diethoxy-2-hydroxypropyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (1 g) in pure formic acid (30 cc) is heated at 50° C. for 40 minutes, diluted with water (3 cc), heated for a further 10 minutes and concentrated to dryness at 30° C. under 0.05 mm Hg. The residue is taken up in acetone (3×30 cc), concentrating to dryness each time at 20° C. under 30 mm Hg, and the solid is then taken up in acetone (50 cc). The mixture is heated under reflux for 10 minutes, whilst stirring, and filtered. The E form of the syn isomer of 7-[2-(2-aminothiazol-4-yl)-(2-methoxyiminoacetamido]-2-carboxy-3-{2-[5,6-dioxo-4-(2-hydroxy-3-oxopropyl)-1,4,5,6-tetrahydro-1,2,4-triazin-3-yl]-thiovinyl}-8-oxo-5-thia-1-azabicyclo[4.2.0]-oct-2-ene (0.6 g) is collected in the form of a yellow powder.

Infra-red spectrum (KBr), characteristic bands (cm⁻¹): 3,405, 3,260, 1,770, 1,710, 1,680, 1,585, 1,530, 1,040, 940 and 700.

EXAMPLE 10

A solution of sodium azide (65 g) in 95% strength ethanol (1,680 cc) is heated under reflux. A solution of 2,2-dimethoxyethyl isothiocyanate (147.2 g) in 95% strength ethanol (320 cc) is added dropwise, with stirring, in the course of 1 hour 30 minutes, and the mixture is heated under reflux for 12 hours. It is then concentrated to dryness at 40° C. under 20 mm Hg (2.7 kPa), the residue is taken up in acetone (600 cc), the mixture is filtered and diethyl ether (1 liter) is added. The crystallisation is started, and a further amount of diethyl ether (2.5 liters) is added. The batch is left at 20° C. for 24 hours and is then filtered. After drying, the sodium salt of 1-(2,2-dimethoxyethyl)-5-mercapto-tetrazole, in the form of the hydrate (208.2 g), is obtained.

Infra-red spectrum (KBr): characteristic bands (cm⁻¹) at 3480, 3220, 2840, 1660, 1400, 1290, 1115, 1070, 1025 and 790.

REFERENCE EXAMPLES 9 TO 12

By following an analogous procedure to that described in Reference Examples 1 to 8, the products according to the invention can be used to prepare the products of the general formula:

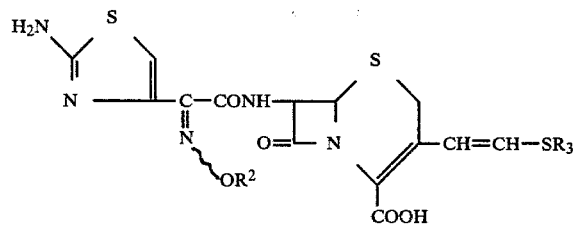

which are identified below:

| Reference Example | R₃ | R² | Stereochemistry | (1) IR spectrum (KBr), characteristic bands in cm⁻¹ (2) Proton NMR spectrum, 350 MHz, CF₃CO₂D, δ in ppm, J in Hz |
| --- | --- | --- | --- | --- |

| Reference Example | R₃ | R² | Stereo-chemistry | (1) IR spectrum (KBr), characteristic bands in cm⁻¹ (2) Proton NMR spectrum, 350 MHz, d₆-DMSO, δ in ppm, J in Hz |
|---|---|---|---|---|
| 9 | CH₂CH(OCH₃)₂ attached to N of triazole ring (N—N=N—N, with CH₃) | —CH₃ | syn isomer, E form | (1) 3,350, 1,780, 1,680, 1655, 1,620, 1,530, 1,120, 1,040 and 940. (2) 3.61 (s, 6H, \C(OCH₃)₂); 3.92 (s broad, 2H, —SCH₂—); 4.31 (s, 3H, =NOCH₃); 4.73 (d, J = 6, 2H, \NCH₂—); 5.0 (t, J = 6, 1H, —CH₂—CH\ ); 5.38 (d, J = 4, H₆); 6.05 (dd, J = 4 and 9, H₇); 7.16 and 7.88 (2d, J = 16, —CH=CH—); and 7.50 (s, H of the thiazole). |
| 10 | triazole with (CH₂)₂NHSO₂CH₃ | —CH₃ | syn isomer, E form | (1) 3,400, 3,300, 3,200, 1,775, 1,710, 1,680, 1,590, 1,530, 1,320, 1,150, 1,140 and 945 (2) 2.90 (s, 3H, —SO₂CH₃); 3.20 (mt, 2H, —CH₂NH—); 3.61 and 3.78 (2d, J = 18, 2H, —SCH₂—); 3.96 (s, 3H, =NOCH₃); 3.96 (t, J = 5, 2H, \N—CH₂—); 5.17 (d, J = 4, 1H, H in the 6-position); 5.73 (dd, J = 4 and 9, 1H, H in the 7-position); 6.74 (s, 1H, H of the thiazole); 6.79 (d, J = 16, 1H, —CH=CHS—); 7.17 (s, 2H, —NH₂); and 9.60 (d, J = 9, 1H, —CONH—) |
| 11 | triazole with (CH₂)₂NHCONHCH₃ | —CH₃ | syn isomer, E form | (1) 3,320, 3,200, 1,775, 1,710, 1,680, 1,635, 1,585, 1,535, 1,040 and 945 (2) 3.30 (m, 5H, —CH₂NH— and \NCH₃); 3.60 and 3.78 (2d, J = 18, 2H, —SCH₂—); 3.85 (s broad, 5H, =NOCH₃ and \NCH₂—); 5.18 (d, J = 4, 1H, H₆); 5.74 (dd, J = 4 and 9, 1H, H₇); 6.09 (t, J = 6, 1H, —NH—CH₂—); 6.74 (s, 1H, H of the thiazole); 6.82 and 7.12 (2d, J = 16, 2H, —CH=CH—); 9.58 (d, J = 9, 1H, —CONH—); 12.52 (s, 1H, =N—NHCO— or =N—N=C—) \| OH |
| 12 | triazole with CH₂CH₂NHCOCH₂NH₂ | —CH₃ | syn isomer, E form | Product obtained as the formate (1) 3,700 to 2,200, 1,765, 1,705, 1,675, 1,610, 1,585, 1,530, 1,035 and 930 (2) 3.2 to 3.6 (m, 8H, —SCH₂—, \NCH₂CH₂N/ and —COCH₂N\ ); 3.85 (s, =NOCH₃); 5.12 (d, J = 4, H₆); 5.67 (dd, J = 4 and 9, H₇); 6.35 (d, J = 16, —CH=CHS—); 6.73 (s, H of the thiazole); 7.15 (s broad, —NH₂); 8.2 (s, H of the formate); 8.6 (m, —CH₂NHCO—); and 9.54 (d, J = 9, —NHCO—) |

We claim:
1. A triazine of the formula:

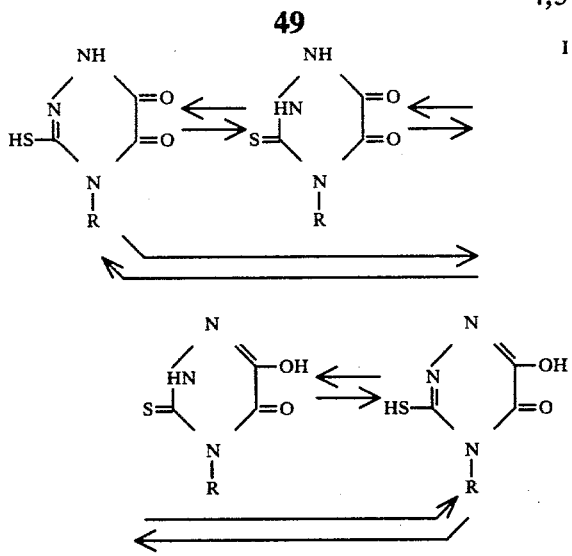

wherein R represents:
(a) 2,2-dimethyl-dioxolan-4-yl methyl or 2,2-dimethyldioxan-5-yl;
(b) $C_2$-$C_4$ alkyl substituted with a member selected from the group consisting of alkylsulphonylamino, sulphamoylamino, alkoxycarbonylamino, ureido, alkylureido, dialkylureido and substituted acylamino wherein the acyl group is substituted with hydroxy, amino, alkylamino, or dialkylamino;
(c) $C_2$-$C_5$ alkyl substituted with alkoxyimino or hydroxyimino;
(d) a radical of the formula:

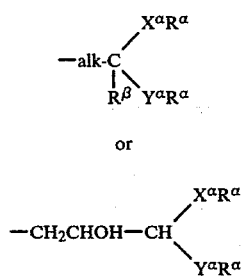

or $$-CH_2CHOH-CH\genfrac{}{}{0pt}{}{X^\alpha R^\alpha}{Y^\alpha R^\alpha}$$  III wherein alk represents $C_1$-$C_4$ alkylene, $X^\alpha$ and $Y^\alpha$ are identical and represent oxygen or sulphur atoms and $R^\alpha$ represents an alkyl radical, or $X^\alpha$ and $Y^\alpha$ are identical or different and represent oxygen or sulphur atoms and the radicals $R^\alpha$ together form an alkylene radical of 2 or 3 carbon atoms, and $R^\beta$ represents $C_1$-$C_3$ alkyl;
(e) carbamoyloxyalkyl, alkylsulphinylalkyl, or alkylsulphonylalkyl in which the alkyl moiety bonded to the triazine grouping in formula I has 2 to 4 carbon atoms;
(f) phenylalkyl or alkylthioalkyl; or
(g) a radical of the formula:

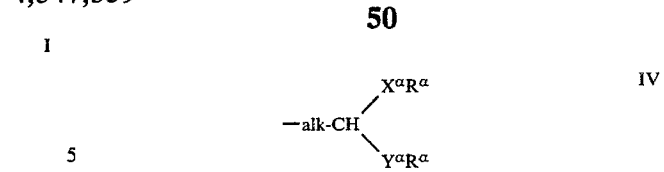

wherein alk, $X^\alpha$, $Y^\alpha$, and $R^\alpha$ are as defined previously, the alkyl and acyl moieties of radicals mentioned above are linear or branched and, unless otherwise specified, contain 1 to 4 carbon atoms, or an alkali metal or alkaline earth metal salt thereof.

2. The compound of claim 1 wherein R represents a carbamoyloxyalkyl, alkylsulphinylalkyl or alkylsulphonylalkyl radical in which the alkyl moiety bonded to the triazine grouping in formula I has 2 to 4 carbon atoms; a phenylalkyl or alkylthioalkyl radical; or a radical of formula IV wherein alk, $X^\alpha$, $Y^\alpha$, and $R^\alpha$ are as defined in claim 1.

3. The compound of claim 1 wherein R is as defined in (a), (b), (c), or (d) in claim 1.

4. The compound of claim 1 wherein R represents 2,2-dimethyldioxolan-4-yl methyl, 2,2-dimethyldioxan-5-yl, an alkyl radical of 2 to 4 carbon atoms, substituted by an alkylsulphonylamino radical, substituted acylamino wherein the acyl moiety is substituted with amino, alkoxycarbonylamino, alkylureido, phenylalkyl, alkylthioalkyl, or a radical of the formula III or IV.

5. The compound of claim 1 wherein R represents 2,2-dimethyldioxolan-4-yl methyl, an alkyl radical of 2 to 4 carbon atoms substituted by an alkoxycarbonylamino radical, phenylalkyl, alkylthioalkyl, or a radical of the formula III or IV.

6. A compound according to claim 1 which is 4-benzyl-5,6-dioxo-3-thioxo-perhydro-1,2,4-triazine or an alkali metal or alkaline earth metal salt thereof.

7. A compound according to claim 1 which is 5,6-dioxo-4-(2-methylthioethyl)-3-thioxo-perhydro-1,2,4-triazine or an alkali metal or alkaline earth metal salt thereof.

8. A compound according to claim 1 which is 4-(2,2-dimethoxyethyl)-5,6-dioxo-3-thioxo-perhydro-1,2,4-triazine or an alkali metal or alkaline earth metal salt thereof.

9. A compound according to claim 1 which is 4-(2,2-diethoxyethyl)-5,6-dioxo-3-thioxo-perhydro-1,2,4-triazine or an alkali metal or alkaline earth metal salt thereof.

10. A compound according to claim 1 which is 4-(2,2-dimethyldioxolan-4-yl-methyl)-5,6-dioxo-3-thioxo-perhydro-1,2,4-triazine or an alkali metal or alkaline earth metal salt thereof.

11. A compound according to claim 1 which is 4-(2-t-butoxycarbonylaminoethyl)-5,6-dioxo-3-thioxoperhydro-1,2,4-triazine or an alkali metal or alkaline earth metal salt thereof.

12. A compound according to claim 1 which is 4-(3,3-diethoxy-2-hydroxypropyl)-5,6-dioxo-3-thioxo-perhydro-1,2,4-triazine or an alkali metal or alkaline earth metal salt thereof.

* * * * *